United States Patent
Arts et al.

(10) Patent No.: US 7,326,387 B2
(45) Date of Patent: *Feb. 5, 2008

(54) AIR DECONTAMINATION DEVICES

(75) Inventors: Theodore A. M. Arts, 312 Countryside La., Williamsville, NY (US) 14221; James M. Thomsen, Key West, FL (US); Paul J. Chirayath, Blesdell, NY (US); Jerome Schentag, Amherst, NY (US)

(73) Assignee: Theodore A. M. Arts, Williamsville, NY (US)

( * ) Notice: Subject to any disclaimer, the term of this patent is extended or adjusted under 35 U.S.C. 154(b) by 547 days.

This patent is subject to a terminal disclaimer.

(21) Appl. No.: 10/434,041

(22) Filed: May 8, 2003
(Under 37 CFR 1.47)

(65) Prior Publication Data
US 2004/0146437 A1    Jul. 29, 2004

Related U.S. Application Data

(60) Provisional application No. 60/382,126, filed on May 20, 2002.

(51) Int. Cl.
*B01J 19/08* (2006.01)

(52) U.S. Cl. .............................. 422/186.3; 422/186.07; 422/121; 96/55

(58) Field of Classification Search ............. 422/186.3, 422/186.07, 121; 96/55
See application file for complete search history.

(56) References Cited

U.S. PATENT DOCUMENTS

| | | | |
|---|---|---|---|
| 2,335,056 A | 11/1943 | Grison | |
| 2,638,644 A | 5/1953 | Rauhut | |
| D193,139 S | 7/1962 | Karp | |
| 3,474,376 A | 10/1969 | Preiss | |
| 3,744,216 A | 7/1973 | Halloran | |
| 3,804,942 A | 4/1974 | Kato et al. | |
| 3,853,529 A * | 12/1974 | Boothe et al. | 55/499 |
| 3,999,964 A * | 12/1976 | Carr | 96/59 |
| 4,017,736 A | 4/1977 | Ross | |
| 4,118,191 A | 10/1978 | Bohnensieker | |
| 4,694,179 A | 9/1987 | Lew et al. | |
| 4,990,311 A | 2/1991 | Hirai et al. | |

(Continued)

FOREIGN PATENT DOCUMENTS

WO    WO 94/06482    3/1994

OTHER PUBLICATIONS

"Filtra 2000 tm. High-Capacity V-Style Absolute Filter," Camfil Farr, Mar. 2002.

(Continued)

*Primary Examiner*—Kishor Mayekar
(74) *Attorney, Agent, or Firm*—Noris, McLaughlin & Marcus

(57) ABSTRACT

Air decontamination devices in one example include a filter directly exposed to ultraviolet ("UV") radiation on an upstream side and a downstream side. Ozone may be provided to permeate the filter, as well. Reflectors may be provided to reflect UV radiation emitted in a direction away from the filter, towards the filter. The filter may be a V-bank filter, for example. Air sampling ports and prefilters may be provided. The air decontamination units may be used to decontaminate the air after industrial and medical contaminations and terrorist biological, chemical and radiological attacks, for example. Mobile isolation units, and methods of decontaminating rooms, are disclosed, as well.

47 Claims, 20 Drawing Sheets

U.S. PATENT DOCUMENTS

| | | | |
|---|---|---|---|
| 5,098,767 A * | 3/1992 | Linnersten | 95/273 |
| 5,112,370 A | 5/1992 | Gazzano | |
| 5,139,546 A | 8/1992 | Novobilski | |
| 5,225,167 A | 7/1993 | Wetzel | |
| 5,230,723 A | 7/1993 | Travis et al. | |
| 5,240,478 A | 8/1993 | Messina | |
| 5,330,722 A | 7/1994 | Pick et al. | |
| 5,453,049 A * | 9/1995 | Tillman et al. | 454/228 |
| 5,593,476 A * | 1/1997 | Coppom | 95/78 |
| 5,601,786 A * | 2/1997 | Monagan | 422/108 |
| 5,616,172 A | 4/1997 | Tuckerman et al. | |
| 5,641,343 A * | 6/1997 | Frey | 96/135 |
| 5,656,242 A | 8/1997 | Morrow et al. | |
| 5,762,667 A | 6/1998 | Pippel et al. | |
| 5,766,455 A | 6/1998 | Berman et al. | |
| 5,837,040 A * | 11/1998 | Caughron et al. | 96/224 |
| 5,837,207 A * | 11/1998 | Summers | 422/121 |
| 5,891,399 A | 4/1999 | Owesen | |
| 5,933,702 A | 8/1999 | Goswami | |
| 5,997,619 A | 12/1999 | Knuth et al. | |
| 6,053,968 A | 4/2000 | Miller | |
| 6,162,118 A | 12/2000 | Arts | |
| 6,245,132 B1 | 6/2001 | Feldman et al. | |
| 6,391,093 B1 | 5/2002 | French et al. | |
| 6,398,039 B1 | 6/2002 | Xue et al. | |
| 6,447,587 B1 | 9/2002 | Pillion et al. | |
| 6,464,760 B1 | 10/2002 | Sham et al. | |
| 6,488,900 B1 | 12/2002 | Call et al. | |
| 6,494,940 B1 | 12/2002 | Hak | |
| 6,508,868 B2 | 1/2003 | Pillion et al. | |
| 6,517,594 B2 | 2/2003 | Olander et al. | |
| 6,579,352 B1 * | 6/2003 | Tanaka et al. | 96/226 |
| 6,616,736 B2 * | 9/2003 | Massey et al. | 96/25 |
| 6,797,966 B2 * | 9/2004 | Summers et al. | 250/492.1 |
| 6,893,610 B1 * | 5/2005 | Barnes | 422/4 |
| 2001/0043887 A1 | 11/2001 | Morneault | |
| 2004/0047776 A1 | 3/2004 | Thomsen | |

OTHER PUBLICATIONS

"PurePleat 40 Pleated Air Filter Media," The Air Sponge Filter Company at http://www.filterfactory.com/filters/pure_pleat_40.html, 1999.

Kowalski et al., "Bactericidal Effects of High Airborne Ozone Concentrations on *Escherichia coli* and *Staphylococcus aureus*," vol. 20, International Ozone Association, pp. 205-221, 1998.

"The New Filtra 2000 Series 1560 Is the Ultimate in High-Capacity HEPA Filtration," Filtra, at least as early as May 20, 2002.

* cited by examiner

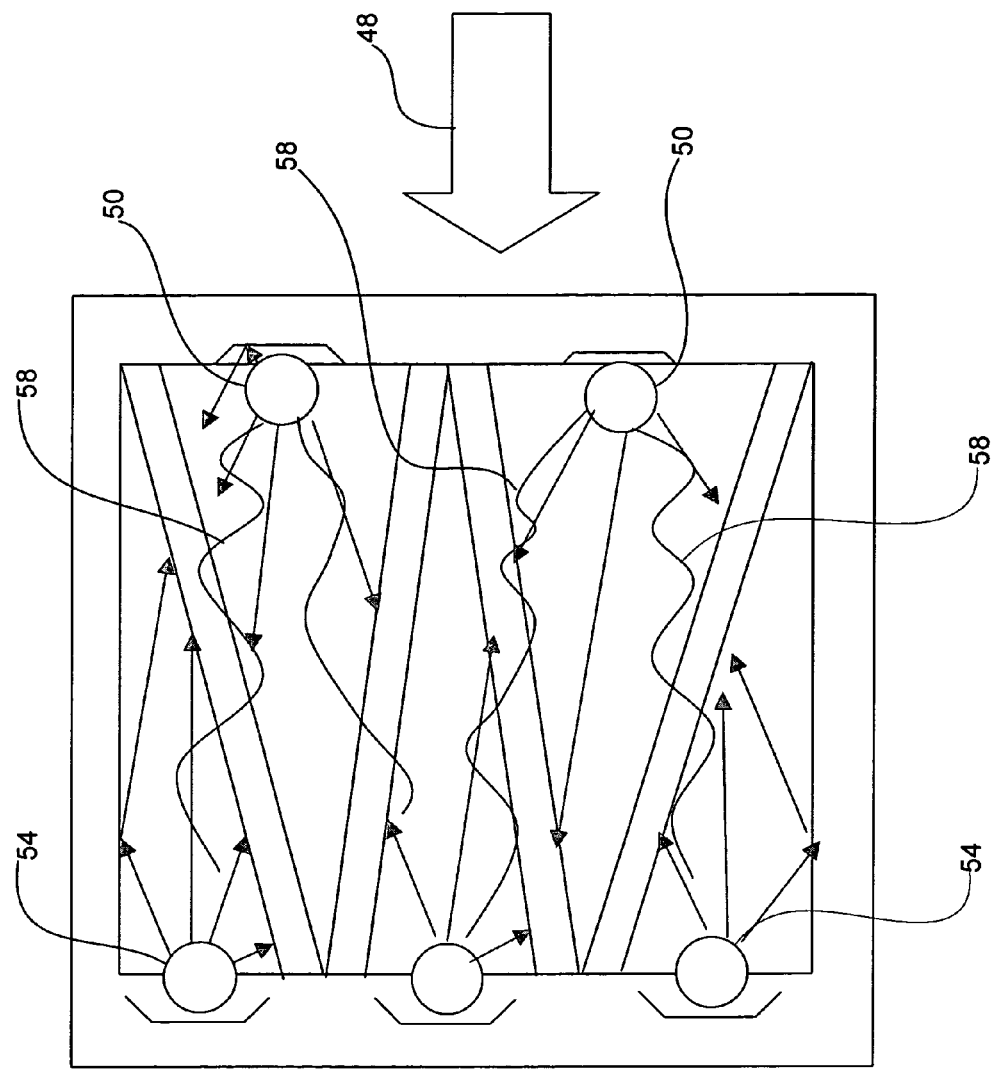
FIGURE 6
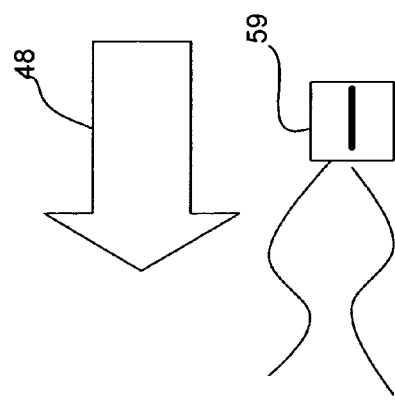

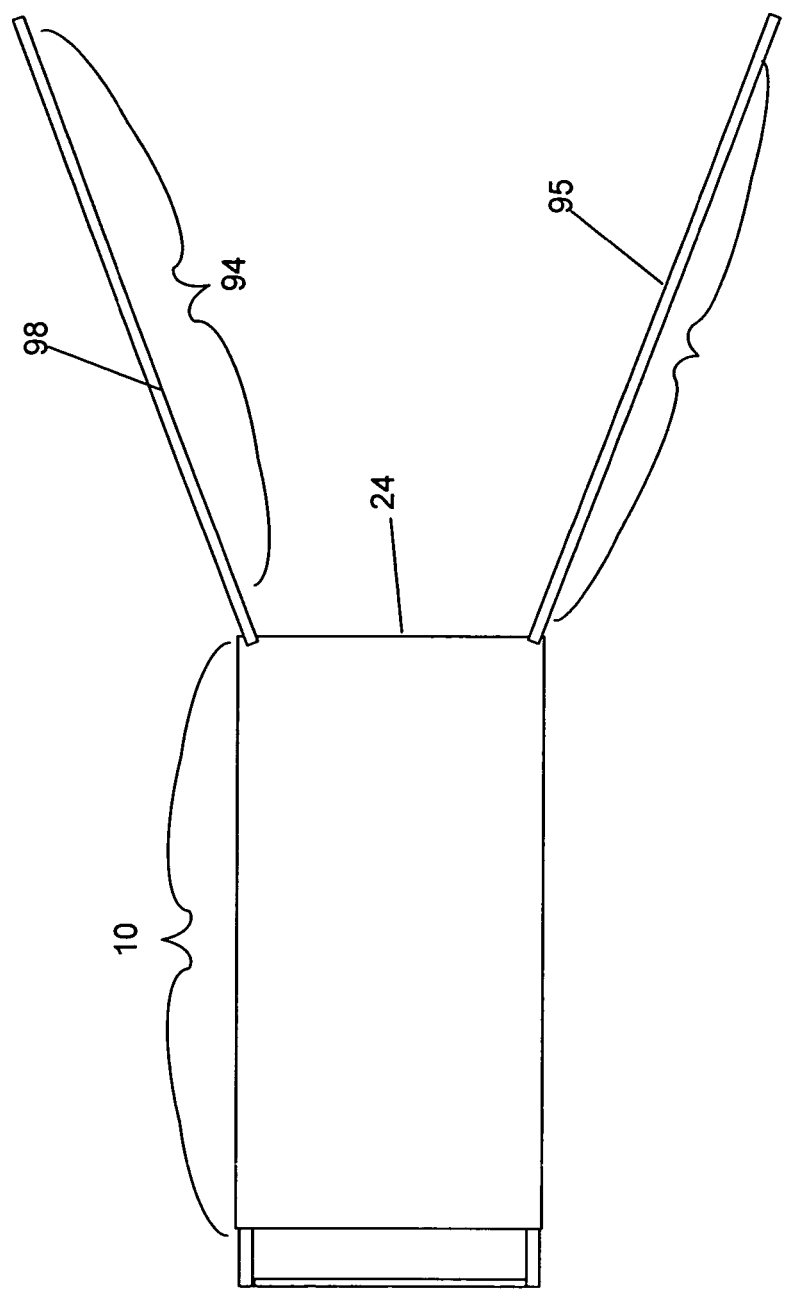

AIR DECONTAMINATION DEVICES

The present application claims the benefit under 35 U.S.C. § 119(e) of U.S. Provisional Patent Application No. 60/382,126 filed on May 20, 2002, which is incorporated by reference, herein.

FIELD OF INVENTION

Air filtration devices and, more particularly, germicidal air filters, decontamination devices and mobile isolation units.

BACKGROUND OF INVENTION

Decontamination devices have typically been designed to filter, irradiate, and/or trap irritants or infectious agents, such as bacteria, viruses, mold and other microorganisms, in air. Such irritants and infectious agents may contaminate the air due to industrial accidents, fires, an infected individual, or a chemical or biological terrorist attack, for example. Decontamination devices typically comprise a chamber to expose contaminated air to ultraviolet ("UV") radiation followed by a filter. The filter may be a high efficiency particle arrester ("HEPA") filter.

Ultraviolet irradiation in prior art devices is typically unable to sufficiently penetrate the filters to kill trapped biological agents. Many biological agents, such as mold and bacteria, can grow on most filter media. The filter media, including such mold and bacteria, as well as trapped viruses, may thereby become a source of contamination and infection. Since some deadly viruses and bacteria can survive for extended periods of time in filters, removal of the contaminated filters may release the very contaminant the decontamination unit was intended to contain. For example, they can cause infection of a person replacing the filter or conducting maintenance on the decontamination device. They may also become a source of infection of people in a room with the device.

In many of these devices, ultraviolet irradiation alone may not provide sufficient decontamination because the contaminated air is not exposed to the radiation for a sufficient time to kill the biological agents. High energy ultraviolet irradiation, such as ultraviolet germicidal irradiation in the wavelength range of 2250-3020 Angstroms ("UVGI"), has been used to irradiate filters but UVGI alone may still not adequately destroy biological agents caught within the filter because in the prior art configurations, the biological agents are not exposed to UVGI irradiation for a sufficient time, and the UVGI irradiation may not adequately penetrate the filter.

U.S. Pat. No. 5,330,722 to Pick et al. ("Pick") provides a UV lamp to expose a surface of a filter to UV irradiation, as the UV lamp and filter are moved with respect to each other. The UV lamp is only exposed to a portion of the filter at any given time. This design may not allow for an adequate germicidal effect upon agents that may pass through portions of the filter that are displaced with respect to the UV lamp. Although Pick suggests providing a UV lamp that is also capable of producing germicidal levels of ozone that can pass through the filter, the ozone and UV are still unable to destroy agents passing through portions of the filter that are not exposed to the UV lamp. Since agents passing through the filter are returned to the air, filtration of the air may be inadequate.

To improve the germicidal effect in a filter, filters have been coated with germicidal agents. For example, in U.S. Pat. No. 5,766,455 to Berman et al., the filter is coated with metal oxide catalysts that are activated by UV light to degrade chemicals and biological agents. Because this requires modifying filters with a metal oxide catalyst slurry, the filters have added expense and require an additional step of quality control to verify that the dynamics of the filter, such as size of particles trapped and maximum air flow, have not been altered.

Isolation rooms, isolation chambers and isolation areas in hospitals, laboratories and manufacturing facilities may filter contaminated or potentially contaminated air and vent the filtered air to a safe area. As above, the filters may become dangerous sources of infection and have to be collected and disposed of accordingly. Mobile isolation units are also known, enabling the expansion of isolation zones in hospitals to facilitate the handling of diseased patients, for example. However, mobile isolation units draw significant amounts of air into the unit, potentially exposing patients to further infection. Since antibiotic resistant strains of bacteria and fungus may be present in hospitals, these isolation units may be dangerous to immune or respiratory compromised patients.

Improved decontamination units and isolation devices are needed to better address typical contamination situations in industrial and medical applications, for example, as well as increasingly dangerous threats posed by antibiotic resistant strains and terrorism.

SUMMARY OF THE INVENTION

In accordance with an embodiment of the invention, a decontamination device is disclosed comprising a housing defining an air inlet, an air outlet and a path for air to flow from the inlet to the outlet. A stationary filter is positioned within the housing, along the path. The filter has an upstream side to receive air flowing along the path and a downstream side for the exit of air from the filter, to the path. At least one first stationary ultraviolet ("UV") lamp is positioned to directly illuminate the upstream side of the filter and at least one second stationary UV lamp is positioned to directly illuminate the downstream side of the filter. An ozone generator is proximate the filter. By providing direct UV illumination of both the upstream and downstream sides of the filter, the UV radiation has greater overall penetration of the filter, enabling the killing of biological agents trapped within or traversing the filter. It is believed that the filter slows the motion of the biological agents, giving the UV radiation more time to act on the agents. In addition, providing the ozone generator proximate the filter allows for ozone to permeate the filter, providing another mechanism for killing biological agents in the filter. The filter may comprise material that is transmissive to ultraviolet radiation, facilitating penetration of the filter by the radiation. The filter thereby becomes an enhanced killing zone. The filter may be sterilized instead of becoming a source of contamination, as in the prior art.

A blower may be provided within the housing, along the path, to cause air to flow along the path during operation. The first and second ultraviolet lamps may completely illuminate the upstream and downstream sides of the filter, respectively. This may further enhance the effectiveness of the UV radiation on and in the filter.

At least one air sampling port may be provided through a wall of the housing of the decontamination unit, to provide communication from an exterior of the housing to the path. The air in the vicinity of the decontamination unit may thereby be drawn through a sampling device in the port, for testing of the air to identify contaminants.

At least one prefilter may be positioned along the path, upstream of the first ultraviolet lamp, such that air flows through the at least one prefilter prior to flowing through the filter, during operation. The prefilter may provide filtration of gases, as well as biological and chemical contaminants, depending on the type of prefilter. The prefilter may be selected based on testing of the contaminated air. The type of prefilter may be selected based on the results of air sampling.

Reflectors may be further provided upstream and downstream of the first and second UV lamps, to reflect UV radiation directed away from the filter, towards the filter. This enhances the intensity of the UV radiation on the filter, improving its effectiveness. The filter may be a V-bank filter and the first and second UV lamps may be partially within the V-shaped regions defined by the filter, to further improve the irradiation of the filter by the UV lamps.

In accordance with an aspect of this embodiment, a method of decontaminating air is disclosed comprising flowing air through a filter having an upstream side receiving air to be filtered and an downstream side from which filtered air exits the filter. The method further comprises illuminating an entire upstream side and downstream side of the filter with ultraviolet light, while the air is flowing through the filter, and permeating the filter with ozone while the air is flowing through the filter.

In accordance with another embodiment of the invention, a decontamination unit is disclosed comprising a housing defining an inlet, an outlet, and a path for air to flow from the inlet to the outlet. A filter is positioned along the path to filter air flowing along the path. The filter comprises a plurality of transverse intersecting walls defining at least one upstream facing chamber to receive air along the path, and a downstream side for air to exit from the filter, to the path. At least one ultraviolet lamp is provided upstream of the filter, facing the at least one chamber, to completely, directly illuminate at least one chamber. A blower may be provided within the housing, along the path, to cause air to flow along the path during operation.

At least one reflector may be provided upstream of the at least one ultraviolet lamp, to reflect ultraviolet light emitted by the at least one ultraviolet lamp, onto the at least chamber. The at least one ultraviolet lamp may be at least partially within a region defined by the chamber. The downstream side of the filter may also define at least one downstream facing open chamber and at least one second ultraviolet lamp downstream of the filter may be provided, facing the at least one chamber, to completely, directly illuminate at least one chamber. At least one second reflector may be provided downstream of the at least one second ultraviolet lamp, to reflect ultraviolet light emitted by the at least one ultraviolet lamp, onto the at least downstream facing chamber. The at least one second ultraviolet lamp may be within a second region defined by the downstream facing chamber, as well. The filter may comprise a plurality of transverse, intersecting walls defining a plurality of upstream and downstream facing V-shaped chambers.

In accordance with an aspect of this embodiment, a method of decontaminating air is disclosed comprising flowing air through a filter that has at least one upstream facing chamber to receive air to be filtered. The method further comprises completely, directly illuminating the at least one upstream facing chamber with ultraviolet light while the air is flowing through the filter. The filter may further comprise at least one downstream facing open chamber and the method may further comprise completely, directly illuminating the at least one downstream facing chamber with ultraviolet light while the air is flowing through the filter. The method may also further comprise permeating the filter with ozone while the air is flowing through the filter.

In accordance with another embodiment of the invention, a decontamination unit is disclosed comprising a housing defining an inlet, an outlet, and a path for air to flow from the inlet to the outlet. A filter is positioned along the path to filter air flowing along the path. The filter has an upstream side defining at least one upstream facing chamber to receive air along the path, and a downstream side for air to exit from the filter, to the path. At least one ultraviolet lamp is provided upstream of the filter, positioned at least partially within a region defined by the chamber, to illuminate the chamber.

In accordance with another embodiment of the invention, a decontamination unit is disclosed comprising a housing defining an inlet, an outlet, and a path for air to flow from the inlet to the outlet. A filter is positioned along the path, to filter air flowing along the path. The housing has an external wall defining an air sampling port through the wall, enabling communication between an exterior of the housing and the path. A blower may be provided within the housing, along the path, to move air from the inlet to the outlet. The blower may be downstream of the filter. The port may be an air sampling port and air may be drawn from the exterior of the housing, through the port, to the path. A sampling tube or a particulate collector may be provided in a port to collect air. A selectable prefilter may be provided along the path, upstream of the filter. The selectable filter may be selected based on air sampling results.

In accordance with an aspect of this embodiment, a method of decontaminating air with a decontamination unit is disclosed comprising flowing air along a path through the unit. The path includes a filter and the air is filtered. The method further comprises collecting an air sample, via the unit. The air sample may be of air external to the unit. A prefilter may be selected based on sampling results, and positioned upstream of the filter in the decontamination unit.

In accordance with another embodiment of the invention, an isolation device is disclosed comprising a frame and a barrier mounted on the frame to partially enclose a space. An air conducting unit is attached to the barrier. The air conducting unit has an air inlet exposed to the enclosed space and an air outlet exposed to an exterior of the device, to conduct air between the partially enclosed space and the exterior of the device, during operation. A recycling vent provides communication from the air conducting unit to a location proximate the enclosed space. The vent may provide communication to a location within or below the space, for example. The frame may be mobile. A blower may be provided within the air conducting unit, to cause air to flow through the air conducting unit from the air inlet to the air outlet. A baffle may be provided within the air conducting unit to deflect at least a portion of the air flowing from the air intake to the air outlet through the air conducting unit out of the recycling vent, during operation. A filter may also be provided within the air conducting unit. Ultraviolet lights and an ozone generator may also be provided. At least a portion of a bed may be received within the partially enclosed space. In accordance with a related embodiment, the isolation device may be an isolation wheelchair.

In accordance with another embodiment of the invention, a method of decontaminating a room is disclosed comprising producing germicidal concentrations of ozone throughout the room, causing air in the room to flow through a filter, from an upstream side of the filter to a downstream side of the filter and illuminating the upstream and downstream sides of the filter with germicidal levels of ultraviolet light.

In accordance with another embodiment of the invention, a method of decontaminating a room is disclosed comprising drawing air from the room through a filter having an upstream side to receive the air and a downstream side for air to exit the filter and illuminating an entire upstream side of the filter with ultraviolet light, while the air is flowing through the filter. The entire downstream side of the filter is also illuminated with ultraviolet light and the filter is permeated with ozone while the air is flowing through the filter. The filtered air is ducted out of the room to create a negative pressure within the room. The room may be a prison cell, for example.

In accordance with another embodiment of the invention, a method of decontaminating a room is disclosed comprising flowing air outside of the room through a filter having an upstream side to receive the air and a downstream side from which the air exits the filter. The entire upstream side and downstream side of the filter is illuminated with ultraviolet light and the filter is permeated with ozone while the air is flowing through the filter. The filtered air is ducted into the room to create a positive pressure within the room.

BRIEF DESCRIPTION OF DRAWINGS

FIG. 6 is a schematic representation of an embodiment of the filter arrangement of FIG. 4, with downstream ozone generators;

FIG. 14a and FIG. 14b show decontamination units as in FIG. 1, with isolation assemblies from a top view and side view, respectively, in accordance with another embodiment of the invention;

DETAILED DESCRIPTION OF THE PREFERRED EMBODIMENTS

Figure 1:
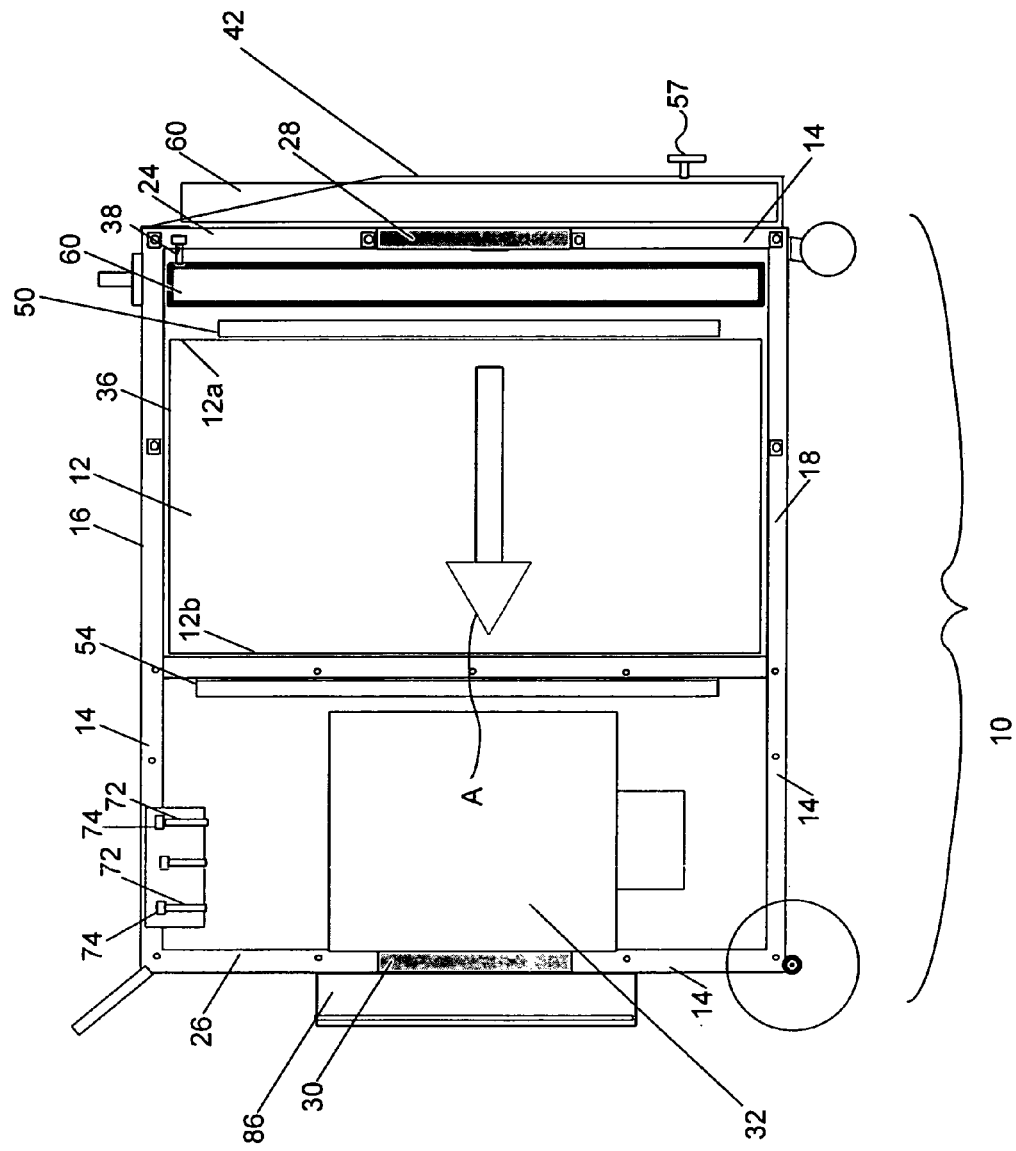
FIG. 1 is a cross sectional schematic diagram of a decontamination unit in accordance with an embodiment of the invention.
Figure 2:
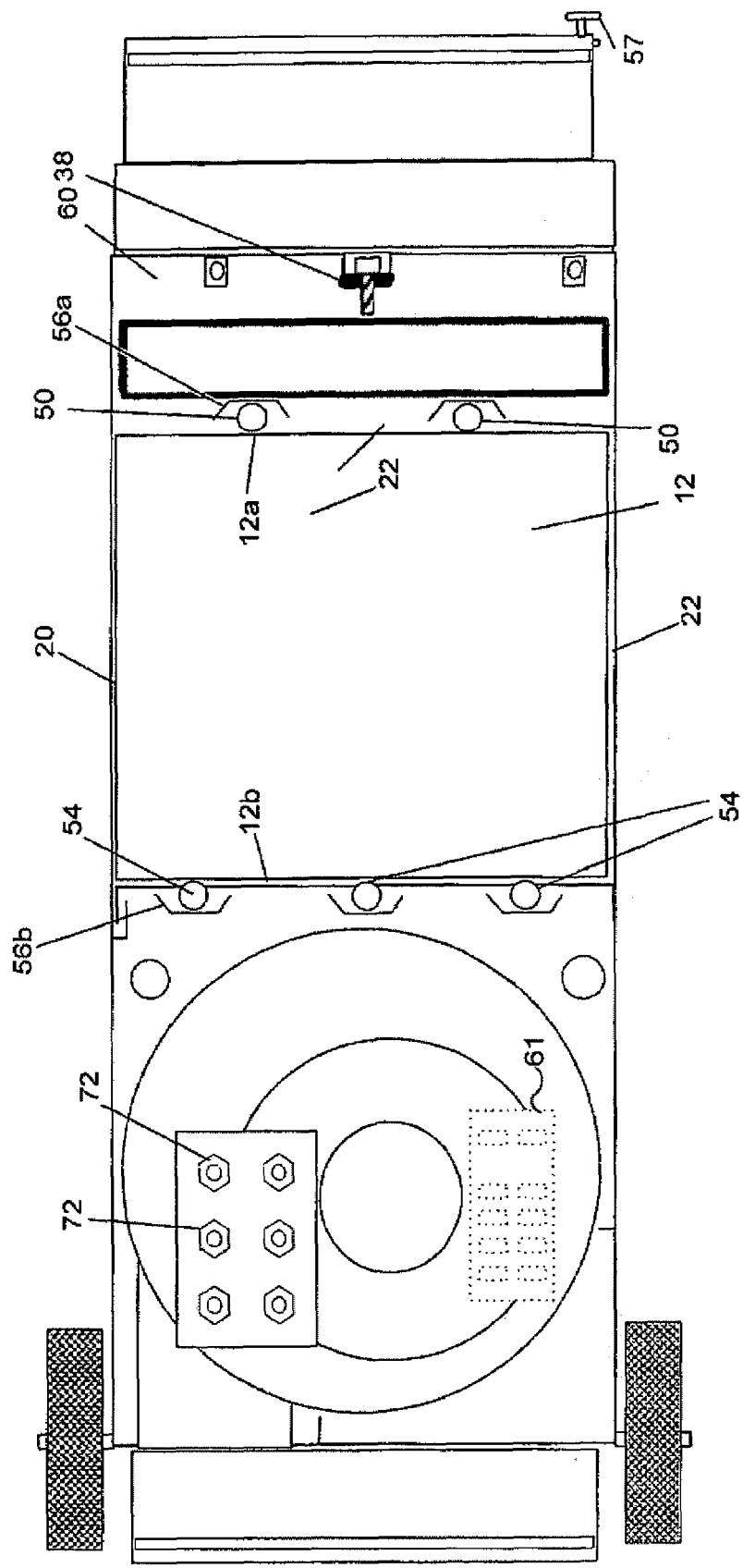
FIG. 2 is a top, cross sectional schematic diagram of the decontamination unit of FIG. 1.

FIG. 1 is a cross sectional schematic representation of a decontamination unit 10 including a filter 12, in accordance with an embodiment of the invention. FIG. 2 is a top cross sectional schematic view of the decontamination unit 10 of FIG. 1. The decontamination unit 10 comprises a housing 14 with a top wall 16, a bottom wall 18, two side walls 20 and 22, a front wall 24 and a back wall 26. An air inlet 28 and an air outlet 30 are defined in the housing 14, in this example in the front wall 24 and the back wall 26. The air inlet 28 and/or the air outlet 30 may be defined in other walls, instead. The housing 14 and structures within the housing define an air path A between the inlet 28 and the outlet 30. The housing 14 is preferably air tight, except for the air inlet 28, the air outlet 30, and optional air sampling ports 72 discussed further, below. The walls of the housing 14 are preferably steel. At least one wall should be removable or hinged to facilitate opening so that elements inside of the housing 14 can be maintained.

Figure 3:
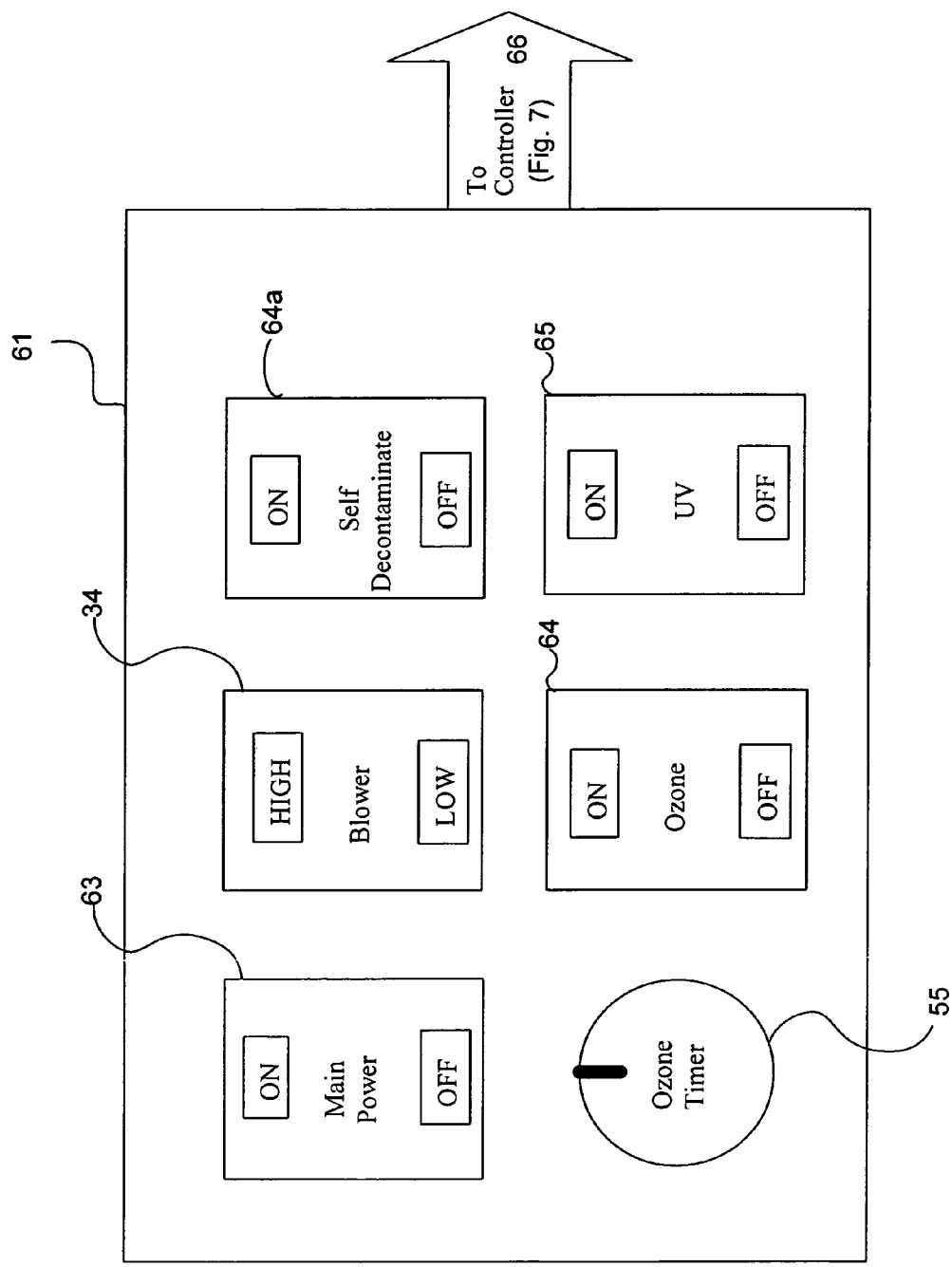
FIG. 3 is an example of a control panel that may be used to operate the decontamination unit of FIG. 1.

In this embodiment, a blower 32 is fixed inside of the housing 14, along the air path A, to draw air into the air inlet 28 path A and to discharge air out of the air outlet 30. A blower 32 is a device for pushing or pulling air. Examples of blowers 32 include, but are not limited to, fans and centrifugal blowers. The blower 32 can be fixed to the housing 14 by standard fasteners such as brackets and bolts or machine screws, for example. The blower 32 preferably has multiple speeds. Preferably, operation of the blower 32 is separately controlled by a switch or dial 34, or other such manually operated control device on the housing surface, as shown in FIG. 3. The blower 32 may be outside of the housing 14, coupled to the air outlet 30, to draw air along path A, as well.

The filter 12 is fixed within the housing 14, along the path A so that the air flowing from the air inlet 28 to the air outlet 30 must pass through the filter 12. The blower 24 may be upstream or downstream of the filter 12 to either push or pull air through the filter. Pulling air through the filter 12 is preferred because cleaner (filtered) air causes less wear on the blower 32 during operation. Preferably, the filter 12 is fixed in a manner that prevents air leakage around the filter, yet allows for removal of the filter during replacement. The filter may be fitted tightly within the housing 14, for example. If the filter 12 does not fit tightly within the housing 14, leakage around the filter may be reduced by a flange welded or fixed to the inside of the housing and extending to the filter 12. A compression clamp or tension screw 38 may be used to fix the filter 12 in place, while allowing for easy removal, for example.

One or more ultraviolet ("UV") lamps 50 are fixed to the housing 14 (or supporting structure within the housing 14). UV lamps 50 are positioned to directly illuminate an upstream side 12a of the filter 12, which receives air to be filtered along the air path A. Preferably, the entire upstream side of the filter 12 is illuminated. One or more UV lamps 54 are also preferably fixed to the housing 14 (or supporting structure within the housing 14), positioned to directly illuminate a downstream side 12b of the filter 12. Filtered air exits the filter 12 from the downstream side 12b.

Reflectors 56a are preferably provided upstream of respective UV lamps 50a, to reflect UV light emitted in a direction away from the upstream side 12a of filter 12, towards the upstream side. Similarly, reflectors 56b are preferably provided downstream of respective UV lamps 54, to reflect UV light towards the downstream side 12b of the filter 12. Preferably, one reflector 56a, 56b is provided for each UV lamp 50, 54.

The ultraviolet lamps 50, 54 preferably provide ultraviolet germicidal irradiation ("UVGI") 52 at germicidal levels at the filter surfaces 12a, 12b. UVGI is in a range of from about 2250 to about 3020 Angstroms for air/surface disinfection and sterilization.

Concentration of UV germicidal irradiation (UVGI) 52 upon the surface of the filter 12 by the reflectors 56 improves the germicidal effect of the UVGI in the filter 12. Examples of germicidal UV lamps include, but are not limited to PerkinElmer Model GX018T5VH/Ultra-V, Perkin Elmer Optoelectronics, Salem, Mass., USA. The ultraviolet lamps 50, 54 and/or the reflectors 56 may be supported by the housing of the decontamination unit 10, as well.

Preferably, filter 12 is a high efficiency filter. In the present invention, a high efficiency filter traps at least 90% of particles of 0.3 microns. More preferably, the high efficiency filter 12 is a high efficiency particle arresting ("HEPA") filter that traps 99.97% of particles at 0.3 microns, 1000 cubic feet per minute ("CFM") (28.32 cubic meters per minute). Most preferably, the filter 12 is an ultra high efficiency particulate arresting ("ULPA") filter that can trap 99.99% of particles at 0.1 microns, at 600-2400 CFM (16.99-67.96 cubic meters per minute). The filter 12 is also preferably fire resistant. Preferably, the fire resistant material is fiberglass, such as a fiberglass mesh, which is also translucent to ultraviolet ("UV") light. Transmission of the UV light into and through the filter 12 is thereby facilitated. UV light passing into and through the fiberglass mesh irradiates pathogens trapped inside of the mesh of the filter 12. The filter 12 used in the embodiments of this invention does not require coating with photopromoted catalysts, although such catalysts may be used if desired.

Figure 4:
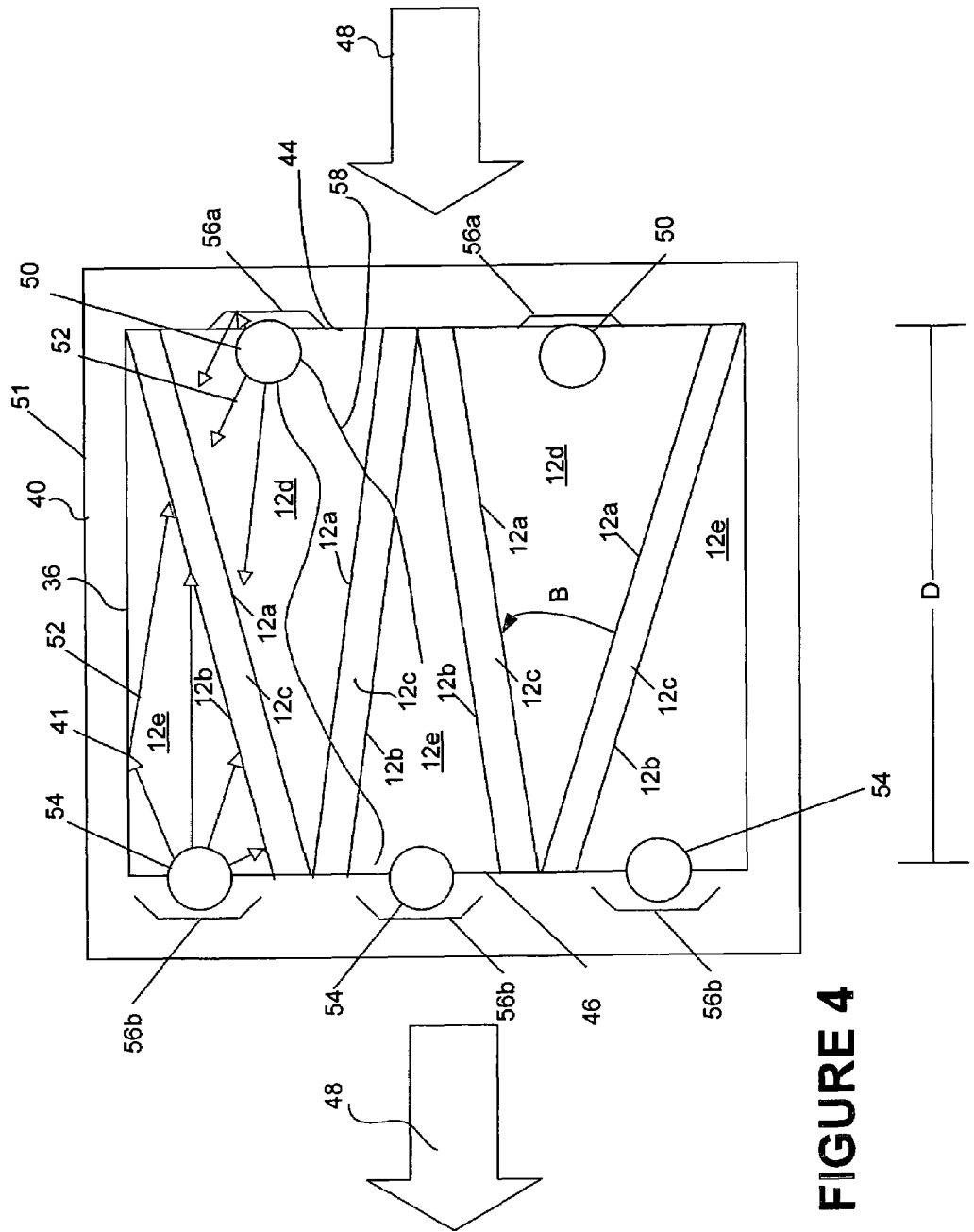
FIG. 4 is a schematic diagram of a preferred filter arrangement in accordance with another embodiment of the invention, which may be used in the decontamination unit of FIG. 1.

FIG. 4 is a cross sectional schematic representation of a preferred filter 12 in accordance with one embodiment of the present invention. In this embodiment, the filter 12 is a V-bank filter comprising a plurality of transverse intersecting walls 12c. The filter 12 is supported in a filter case 36 with a top and bottom walls and two side walls. Preferably, a surface 41 of the filter case 36 facing the filter mesh is reflective to UV light. For example, the surface 41 may be aluminum. Air flow 48 enters the upstream side 44 of the air filter 12 and exits the downstream side 46 of the filter 12. The transverse intersecting walls 4c define upstream facing, open faced chambers 12d. Downstream facing, open faced chambers 12e are defined by the walls 12c and the filter walls of the casing 36. The open faced chambers 12d, 12e may be defined by a filter wall or walls having other configurations, as well.

In this example, the open-faced chambers 12d, 12e define transversely extending V-shaped regions. Each V-shaped region may extend over an arc B of about 30 degrees. The depth D of the V-shaped regions may be about 11⅜ inches (0.23 meters), for example. It is believed that the filter 12 slows the movement of contaminants, providing more time for biological agents to be killed by the UV irradiation and ozone, if provided, in the filter.

The V-bank filter may be one of several Camfil Farr Filtra 200.0™ filters available from Camfil Farr, Inc., Riverdale, N.J., for example. In the description of the Camfil Farr Filtra 2000™ filters provided herein, the information is that provided in literature by Camfil Farr, Inc. The Camfil Farr Filtra 2000™ filters discussed below comprise micro-glass fiber in an acrylic resin binder. The filters have a pleat depth of 27.5 millimeters.

The Camfil Farr Filtra 2000™ Model No. FA 1565-01-01, which may be used in a decontamination unit 10 with an airflow of 700 CFM (19.82 cubic meters per minute), for example, has a 99.99% efficiency at 0.3 microns, when evaluated according to the IEST Recommended Practice. It has a rated check airflow of 900 CFM (25.48 cubic meters per minute). The resistance at rated airflow is 1.0 inches w.g. The media area is 174 square feet (16.16 square meters). The dimensions of the filter are 24 inches×24 inches×11.50 inches (length×height×depth) (0.61 meters×0.61 meters×0.29 meters).

The Camfil Farr Filtra 2000™ Model No. FA 1560-01-01 may be used in the decontamination unit 10 with an airflow of 2,000 CFM (56.63 cubic meters per minute), for example. This model filter has a rated airflow of 2400 CFM (67.96 cubic meters per minute). The dimensions and resistance at airflow of the filter are the same as that of the filter for the Camfil Farr Filtra 2000™ Model No. FA 1565-01-01 filter rated at 900 CFM (25.48 cubic meters per minute), discussed above. The media area is said to be 431 square feet (40.04 square meters).

Camfil Farr 2000™ Model Nos. FA 1565-02-01 and FA 1560-02-01, which are ULPA filters providing 99.999% efficiency at 0.3 microns and 99.99% efficiency at 0.1 microns, may be used, as well. The dimensions and resistance at airflow of these models and the models described above are the same. The FA 1565-02-01, which has the same media area as the FA 1565-01-01 discussed above, has an airflow of 693 CFM (19.62 cubic meters per minute) and may be used in a decontamination unit 10 with an airflow of about 700 CFM (19.82 cubic meters per minute), for example. The FA 1565-02-01, which has the same media area as the FA 1560-01-01, has an airflow of 1848 CFM (52.33 cubic meters per minute) and may be used in a decontamination unit 10 with an airflow of about 2000 CFM (56.63 cubic meters per minute), for example.

Another example of a V-bank high efficiency filter is the Flanders Model SF2K-5-G2-CG available from Total Filtration Solutions Inc., Grand Island, N.Y.

The UV lamps 50 upstream of the filter 12 and the UV lamps 54 downstream of the filter 12 are shown in FIG. 2. Preferably, the UV lamps 50 and 54 are positioned to completely and continuously illuminate the mesh surfaces of the upstream side 12a and downstream side 12b of the filter 12, respectively, during operation. The UV lamps 50, 54 are preferably located at least partially within the upstream facing chambers 12d and the downstream facing chambers 12e defined by the transverse intersecting walls 12c of the V-bank filter 12. The reflectors 56a, 56b are shown, as well, outside of the chambers 12d, 12e but close to the UV lamps 50, 54.

The upstream UV lamps 50 may also be ozone generating lamps. The air flow 48 pulls the ozone 58 through the filter 12, increasing the germicidal effect through the filter. The entire filter 12 may then become a germicidal killing zone through its entire depth. Additionally, ozone facilitates the breakdown of odorants and some toxic gases, further decontaminating the air passing through the filter 12. The downstream lamps 54 may be ozone generators, as well. An example of an acceptable ozone generating UV lamp is a Model GX018T5L/Ultra-V manufactured by Perkin Elmer Optoelectronics, Salem, Mass. 01970 USA.

Figure 5:
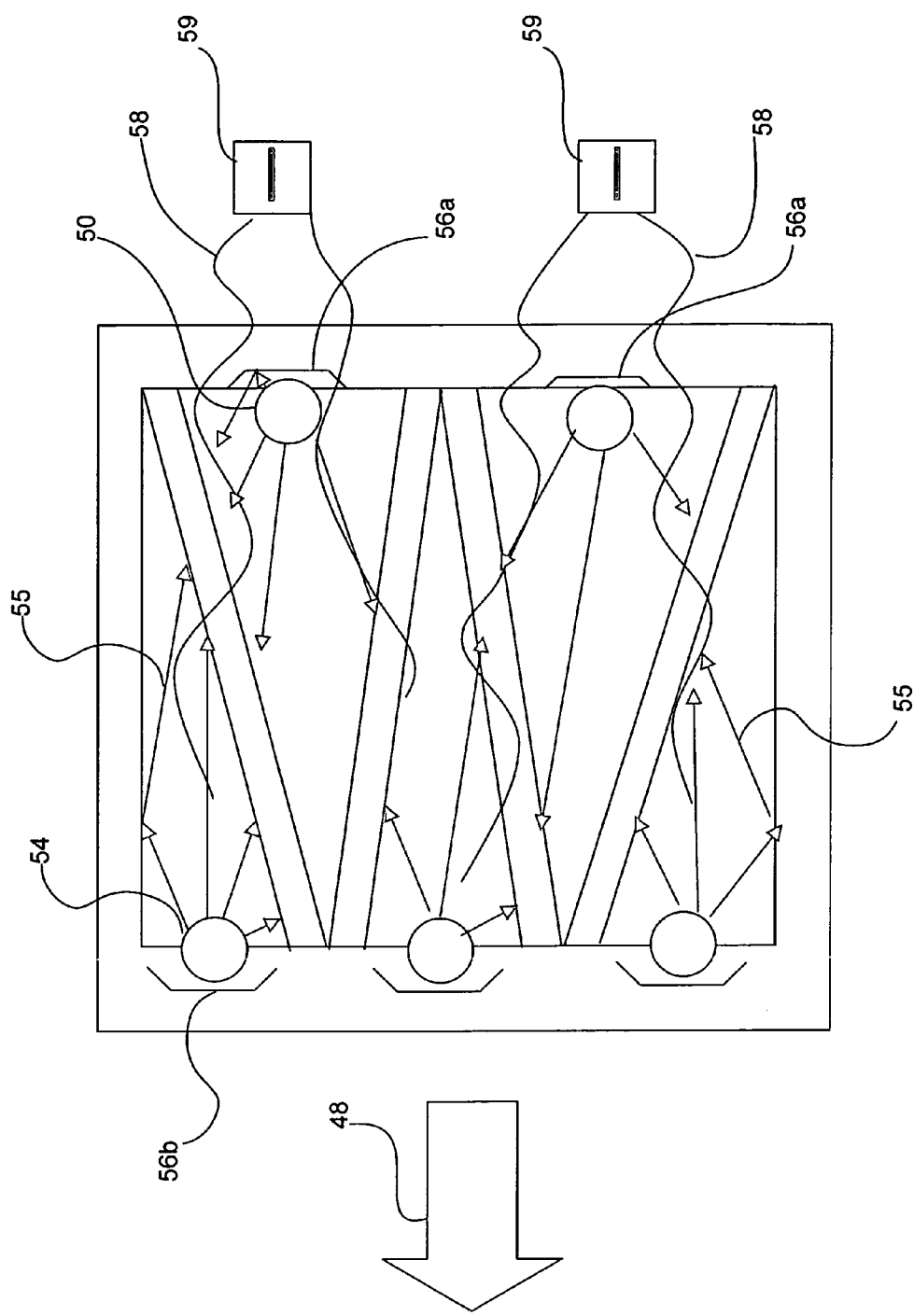
FIG. 5 is a schematic diagram of another embodiment of the filter arrangement of FIG. 4, including upstream ozone generators.

Alternatively, the ozone generator need not be a UV lamp 50. Many types of ozone generators, such as corona wires, are known and readily available. One or more ozone generators 59 may be fixed to the filter case 36 of the filter 12 or to the housing 14 of the decontamination unit 10, upstream of the filter 12, so that the filter 12 is saturated with germicidal concentrations of ozone during operation, as shown in FIG. 5. While it is preferred that the ozone generator 59 be upstream of the filter 12, it may be provided downstream, as shown in FIG. 6.

Optimal placement of a UV lamp 50 and 54 and ozone generator 50 and/or 59 to provide a germicidal effect on and within the illuminated filter 12 requires knowledge of the UV light intensity of the lamps 50 and 54 and rate of ozone production by the ozone generator 50. The following equations provide guidance for calculating the germicidal effect of UV lamps and ozone generators at a given distance.

A surviving microbial population exposed to UV irradiation at wavelength o 254 nanometers ("nm") is described by the characteristic logarithmic decay equation:

$$\ln[S(t)] = -K_{UV}I_{UV}t$$

where $k_{UV}$=standard decay-rate constant, (cm²/microW-s)

$I_{UV}$=Intensity of UV irradiation, (microW/cm²)

t=time of exposure, (sec)

The standard decay rate constant k defines the sensitivity of a microorganism to ultraviolet irradiation. This constant is unique to each microbial species. The following table demonstrates the effect of ultraviolet irradiation on survival of selected microbes.

TABLE I

| Organism | Group | Percent Reduction | Intensity (microW/cm²) | Time (sec) |
| --- | --- | --- | --- | --- |
| Vaccinia | Virus | 99% | 25 | 0.02 |
| Influenza A | Virus | 99% | 25 | 0.02 |
| Coxsackievirus | Virus | 99$ | 25 | 0.08 |
| Staphylococcus aureus | Bacteria | 99% | 25 | 1.5 |
| Mycobacterium tuberculosis | Bacteria | 99% | 25 | 1.9 |
| Bacillus anthraci | Bacteria | 99% | 25 | 3.6 |

A surviving microbial population exposed to ozone is described by the characteristic logarithmic decay equation:

$$\ln[S(t)] = -K_{O3}I_{O3}t$$

where $k_{O3}$=standard decay-rate constant, (l/mg-s)

$I_{O3}$=Concentration of Ozone, (mg/l)

t=time of exposure, (sec)

The standard decay rate constant k defines the sensitivity of a microorganism to ozone. As in the use of ultraviolet irradiation, the ozone survival constant is unique to each microbial species. The following table demonstrates the effect of ozone on survival of selected microbes.

TABLE II

| Organism | Group | Percent Reduction | Concentration (mg/l) | Time (sec) |
| --- | --- | --- | --- | --- |
| Poliomyetis virus | Virus | <99.99% | 0.3-0.4 | 180-240 |
| Echo Virus 29 | Virus | <99.99% | 1 | 60 |
| Streptococcus sp | Bacteria | <99% | 0.2 | 30 |
| Bacillus sp | Bacteria | <99% | 0.2 | 30 |

Germicidal concentrations of ozone at a given distance from an ozone generator 54 can be determined and the ozone generator 54 can be positioned within that distance from the filter 18. To verify the location of the ozone generator 54, the concentration of ozone at the surface of the filter 12 can be measured by ozone detectors. The multispeed blower 32 can be set for air flow rates adequate to saturate the filter 12 with germicidal levels of ozone while still providing a high CFM of air flow for rapid turn over rates of air in the area being decontaminated. A preferred range is from about 600 to about 2000 CFM (16.99-67.96 cubic meters per minute).

Embodiments of the invention that include ozone generators 50, 59 may also have UV lamps 54 downstream of the filter 12 that produce UV radiation 55 at wavelengths that facilitate the breakdown of ozone. Ultraviolet radiation in the UV "C" spectrum may be used. 255.3 nanometers is an effective wavelength, to break down ozone, for example. Accordingly, sufficient ozone can be produced at germicidal concentrations within the filter 12 while OSHA acceptable levels of ozone (less than 0.1 ppm) are released with the purified air through the outlet 30.

It may also be desirable to flood a contaminated room or space, which would typically have been evacuated, with ozone for further decontamination and odor reduction. Ozone generators 50 and/or one or more additional ozone generators 59 supported in the housing along the air path A may be used to produce ozone that is exhausted from the unit 10 through the outlet 30, into the room or space. In this case, if the UV lamps 54 emit radiation in a range that would break down ozone, they would not be turned on. The UV lamps 54 that break down ozone may be controlled by a separate switch or other such manual control device than that controlling the UV lamps 50, so that operation of the UV lamps 54 may be separately controlled.

Additionally, an ozone detector 57 may be provided on the unit 10 to monitor ozone levels in the air. The ozone detector 57 may be supported on the exterior of the housing 14, proximate to the air inlet 28, for example. The ozone detector 57 may be coupled to a control circuit, discussed below with respect to FIG. 7, that turns off power to the ozone generator 54 if the ozone level exceeds a predetermined level. If the unit 10 releases purified air and trace ozone in occupied areas, the preferred ozone level for shut off is the OSHA accepted level of 0.1 ppm ozone. The most preferred level for triggering shut off of ozone generation is 0.05 ppm ozone, especially if the unit is used in a hospital environment. The ozone detector 57 could also be used to maintain a desired level of ozone in a room or area. For example, if the ozone level detected by ozone detector 57 drops below a desired level, power to the ozone generator 54 and/or 59 could be turned on again. The ozone detector 57 may be an OS-1X Low Concentration Ozone Switch available from Applied Ozone Systems, Auburne, Calif., for example, which acts like an ozone level "thermostat".

A timer 55 may also be provided to set the amount of time the ozone generators 50 and/or 59 operate. The timer 55 is shown schematically in FIG. 3 and FIG. 7.

Figure 7:
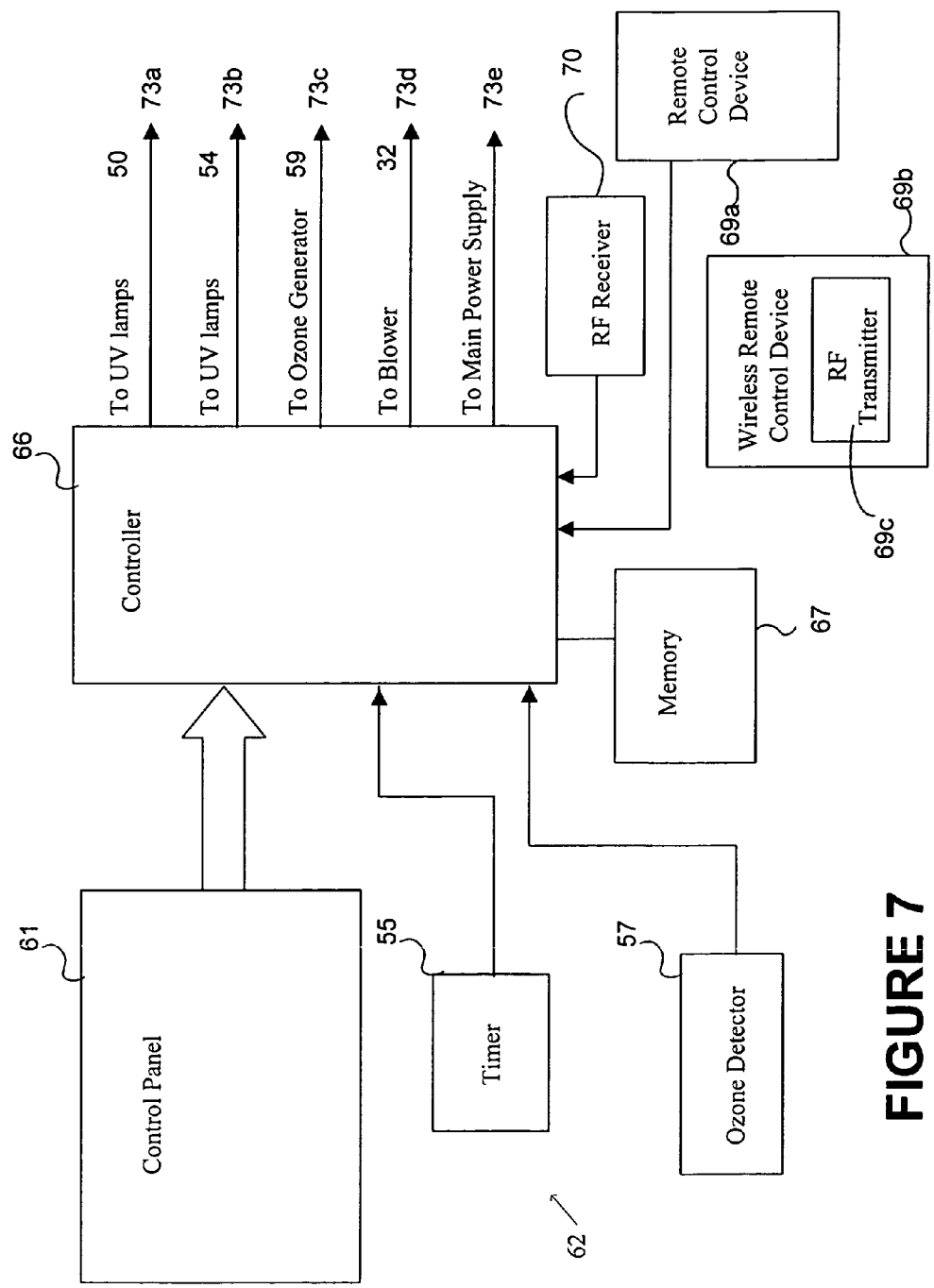
FIG. 7 is an example of a control circuit that may be used to control operation of the decontamination unit of FIG. 1.

FIG. 3 is a schematic diagram of an example of a control panel 61 that may be used to operate the decontamination unit 10 and FIG. 7 an example of a control circuit 62 for controlling operation of the decontamination unit 10. Manually operated control devices 34, 63, 64, and 65, which may be push buttons, switches or dials, for example, are provided to control the blower 32, main power to the unit 10, the ozone generators 59 and the UV lamps 50, 54, respectively. The separate control devices 34, 63, 64 and 65 may be coupled to a controller 66, which may be a processor, such as a microprocessor, or a relay board, for example, as shown in FIG. 7. If the controller 66 is a microprocessor, memory 67 may be provided to store a program to control operation of the decontamination unit 10, based, at least in part, on inputs provided by the control devices and other optional inputs, discussed below. If the controller 66 is a relay board, the relay board acts as an interface between the control devices in the control panel 61 and the other optional inputs discussed below, and the respective components of the decontamination unit 10 being controlled. Separate control devices may be provided in the control panel 61 for the UV lamps 50 and the UV lamps 54, as well.

The optional inputs may include timer 55 and/or the ozone detector 57, if provided, as shown in FIG. 7. The controller 66 has outputs 73a, 73b, 73c, 73d, 73e to the UV lamps 50, the UV lamps 54, the ozone generator 59, the blower 32, and the main power supply (not shown), respectively.

The controls on the decontamination unit 10 may also be remotely controlled. For example, an operator may have the option to control operation of the decontamination unit 10 with a remote control device 69a, which may be a hand held control device or a computer terminal, for example, that is coupled electrically via wires to a controller 66. A wireless remote control device 69b may also be used. The wireless remote control device 69b may include a radio frequency ("rf") transmitter 69c and an rf receiver 70 may be coupled to the controller 66. Either option enables an operator to control operation of the decontamination unit 10 from another, safe room or other location. If a remote control is not provided, the length of time of operation of the decontamination unit 10, the length of time that ozone is generated, and a delay to the start of operation, for example, may be set or programmed to provide time for the operator to leave the vicinity of the unit 10.

Decontamination of any element of the decontamination unit 10 itself after operation may be provided by generating ozone from the ozone generators 50 and/or 59 without operating the blower 32. Decontamination unit 10 would then become flooded with ozone, decontaminating components of the unit along the air path A. An additional control device 64a for self-decontamination of the unit may control the blower 32, the ozone generators 50 and/or 59 and the UV lamps 54 (if operation of UV lamp 54 may cause the breakdown of ozone). The controller 66 may be programmed or hard wired to respond to activation of control 64a by turning on the ozone generator 50 and/or 59, turning off the blower 32 and turning off the UV lamp 54, if necessary.

The decontamination unit 10 may have a prefilter 60 attached to the housing 14 upstream of the UV lamps 50. The prefilter 60 may remove gases. It may also provide an initial filtration of larger particles, for example, facilitating subsequent filtration and sterilization by the filter 12. Use of a prefilter also helps protect the upstream UV lamps 50 from accumulation of contaminants. The prefilters may be supported in a sleeve 42 framing the air inlet 28 and/or may be fixed within the housing downstream of the air inlet and upstream of the UV lamps 50. Both options are shown in FIG. 1. Choice of the prefilter 60 may depend upon the type(s) of contaminants in the air.

The prefilter may comprise activated carbon, which has a large surface area and tiny pores that capture and retain gases and odors. Activated carbon filters are readily commercially available. Activated carbon filters may be obtained from Fedders Corporation, Liberty Corner, N.J., for example.

Another commercially available prefilter that may be used may comprise zeolite, which is a three dimensional, microporous, crystalline solid with well defined structures that contain aluminum, silicon and oxygen in their regular framework. The zeolite is thermally bonded to a polyester to form the filter medium. Volatile organic compounds and gases become trapped in the void porous cavities. Zeolite is especially useful in removing ammonia and ammonium compound odors such as pet odors and urine.

Other commercially available prefilters and prefilter materials include BioSponge, PurePleat 40, MicroSponge Air Filters™, and electrostatic filters, for example. Additional types of prefilters are well known in the art and readily available, as well. Other suppliers of filters that may be used as prefilters include Flanders Precisionaire, St. Petersburg, Fla. and www.dustless.com, for example. The dimensions of the prefilter 60 may be 24 inches×12 inches×2 meters (length×height×depth) (0.61 meters×0.30 meters×0.05 meters), for example.

Figure 8:
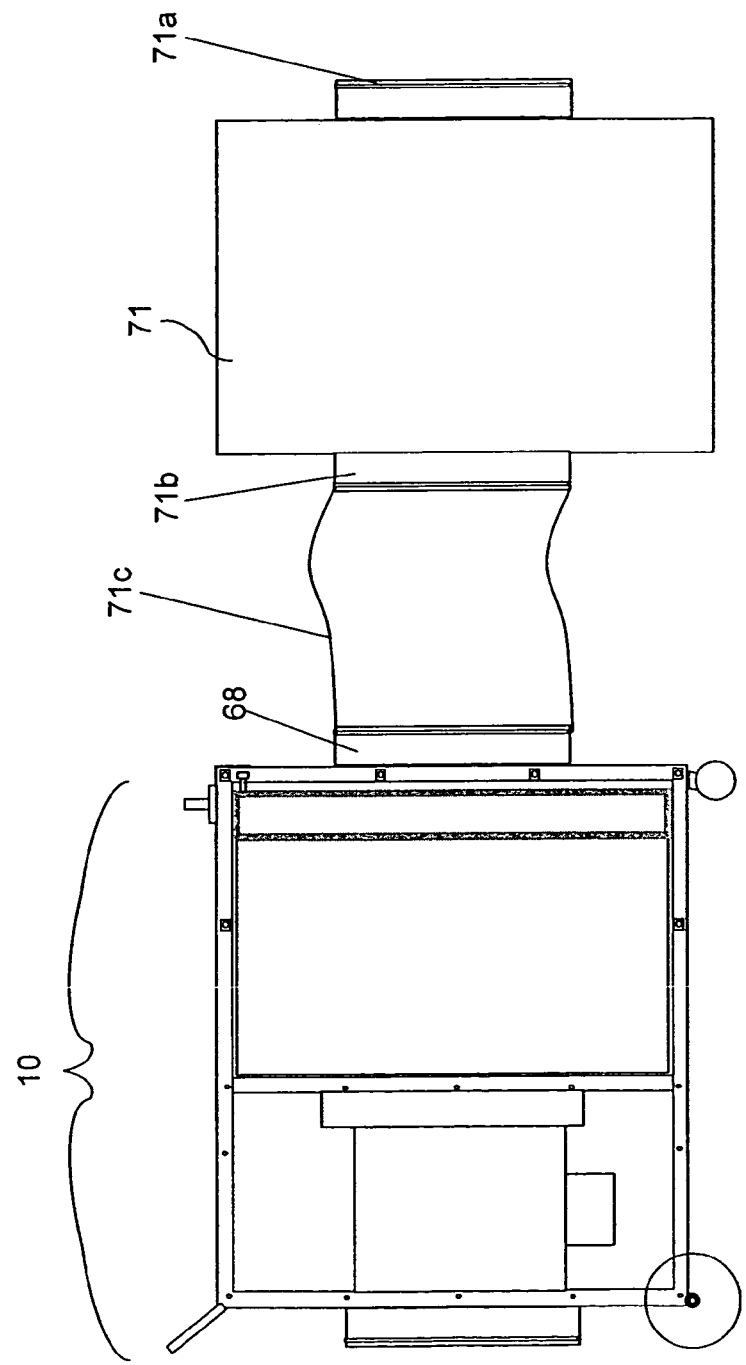
FIG. 8 is a cross sectional diagram of the decontamination unit of FIG. 1 connected to a High Efficiency Gas Absorber (HEGA) module.

In accordance with another embodiment of the invention, a High Efficiency Gas Absorber ("HEGA") module 71 may be coupled to the decontamination unit 10 as a prefilter, as shown in FIG. 8. The HEGA module 71 may be used as a gas phase scavenger to absorb nuclear, biological, or chemical (NBC) gases, for example. The HEGA module 71 has an air inlet 71a and an air outlet 71b. The air outlet 71b can be coupled to a duct adapter 68 that may be attached to the outside surface of the decontamination unit 10, in front of the air inlet 28. Operation of the blower 32 will pull air into the air inlet 71a of the HEGA module 71, through the HEGA module 71, out of the air outlet 71b of the HEGA module 71 and into the air inlet 28 of the decontamination unit 10. Optionally, a duct 71c can be placed between the duct adaptor 68 of the decontamination unit 10 and the second air outlet 71b of the HEGA module 71. HEGA modules are particularly effective prefilters of gaseous contaminants. A HEGA module 71 may also be attached to an outlet duct adapter 86 connected to an outside surface of the unit 10, framing the outlet 30 of the unit, in addition to or instead of attaching a HEGA module to the inlet duct adapter 68, to absorb gases that may have penetrated through the decontamination unit 10.

An example of a HEGA filter that may be used is a RS12 filled with AZM/TEDA for Warfare/Nuclear Carbon, available from Riley Equipment Co, Houston, Tex. AZM/TEDA is a composition of activated tetra-charcoal and additives dependent on the particular contaminant of concern, which is also provided by Riley Equipment Co. HEGA filters may also be obtained from Fedders Corporation, Liberty Corner, N.J., for example.

Figure 9:
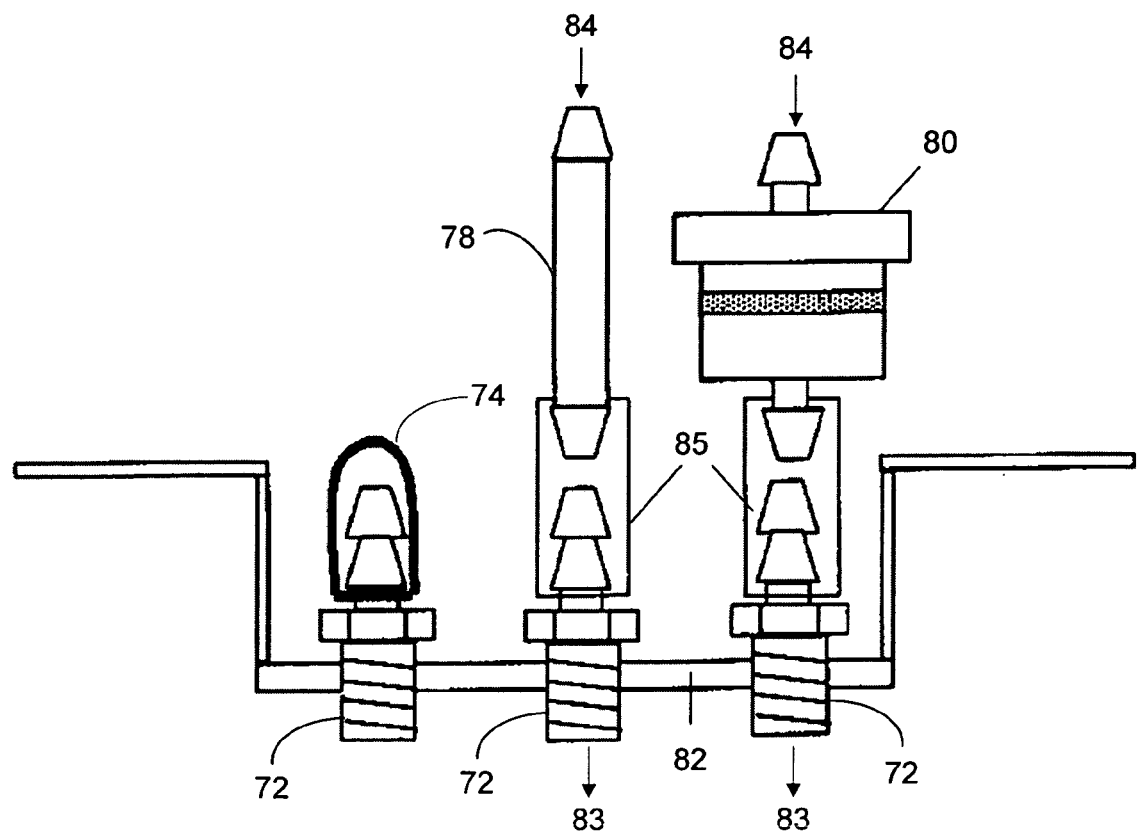
FIG. 9 is a cross sectional schematic diagram of a portion of the housing of the decontamination unit of FIG. 1, showing sampling ports.

One or more air sampling ports 72 may be provided through the wall 82 of housing 14 of the decontamination unit 10, to enable sampling of the air being drawn through the unit 10 to identify contaminants and to determine if contamination levels have been sufficiently reduced, as shown in FIGS. 1 and 2. FIG. 9 is a partial cross-sectional view of a portion of the housing 14, showing the air sampling ports 72 in more detail. The ports 72, which may have open ends, may be provided with a rubber cap 74 to close the port when not in use. An air sampling tube 78 and/or a particulate collector 80 may be inserted into a sampling port 72, as shown in FIG. 9. The ports 72 are designed to receive standard sampling tubes 78 and standard particulate collectors 80. An adapter 85 may be attached to the port 72, to receive the sampling tube 78 or particulate collector 80, after removal of the cap 74.

Preferably, a series of air sampling ports 72 span the housing so that an operator of the decontamination unit 10 can simultaneously test for multiple hazardous gases and particulates. During operation of the decontamination unit 10, the vacuum 83 created by the blower 32, causes air 84 exterior to the unit 10 to be drawn through the sampling tube 78 and particulate collector 80, into the air path A of the unit 10.

As mentioned above, the blower 32 is preferably located downstream of the filter 12 to draw air through the filter 12. A strong vacuum is thereby created downstream of the filter 12. Operation of the air sampling ports 72, which span the housing 14 downstream of the filter 12 and upstream of the air outlet 30, benefit from the stronger vacuum in this preferred configuration. The blower 32 may be upstream of the filter 12 and blow air downstream, through the filter 12 and past the air sampling ports 72, as well.

Air sampling glass tubes 78 are typically designed to detect one specific chemical. The operator typically first breaks both ends of the glass tube 78 to allow air to flow through the tube, and then inserts the tube into an open end of the adapter 84 on an air sampling port 72. There are many different types of commercially available calorimetric sampling tubes. Another type of air sampling tube is a Sorbant air sampling tube, which draws suspect material in the air into a material such as carbon. A tube with suspect contaminants may be provided to a laboratory that flushes and analyzes the contents to identify air borne contaminates.

Particulate collectors 80 sample for dusts and particulates. Quantitative assessment of contaminants in a particulate collector 80 requires calculation of the amount of drawn air. A rotameter may be used, for example, as known in the art. Concentration of contaminants at a low concentration may only be detected in concentrated samples created by drawing sufficient volumes of air through the collector and then determining the rate of flow by using the rotameter. Particulate collectors 80 use special materials that dissolve and allow the laboratory to measure the captured contaminates, as is also known in the art.

Air sampling techniques are well known and there are many types of tubes, samplers and air sampling equipment commercially available, as is known in the art. Air sampling guides are available from the Occupational Safety and Health Administration (OSHA), the Environmental Protection Agency (EPA), and the National Institute for Occupational Safety and Health (NIOSH), via the Internet, for example.

The embodiments of the decontamination unit 10 of the invention are particularly suited for use in industrial and medical contaminations, which may include chemical, biological and radiological accidents. The decontamination unit 10 of embodiments of the present invention may also be used after biological, chemical and radiological terrorist attacks. Detection of what is and also what is not present at a site of contamination is particularly important after a terrorist attack. Some biological and chemical agents and weapons may be deadly at very low concentrations. Having sampling ports 72 that assist in analyzing the air at a contaminated site may therefore be useful in determining the optimum approach to decontamination, including choice of prefilter, whether or not to use ozone, and required remediation time to achieve adequate decontamination, after terrorist attacks, as well as industrial and medical contaminations.

Adequate time for remediation is usually given in number of times the air in an area has passed through the decontamination device 10 or "air changes". For example, nuisances like dust or pollen in a room require 2 to 4 air changes of the entire volume of air in the room. Typically, the more deadly the contaminant, the more air changes are required. Toxins, including but not limited to asbestos, certain gases, and most infectious material, may require 4-8 air changes. Extremely dangerous or deadly agents, such as smallpox, anthrax, chlorine dioxide, for example, may require 8-12 air changes.

Figure 10:
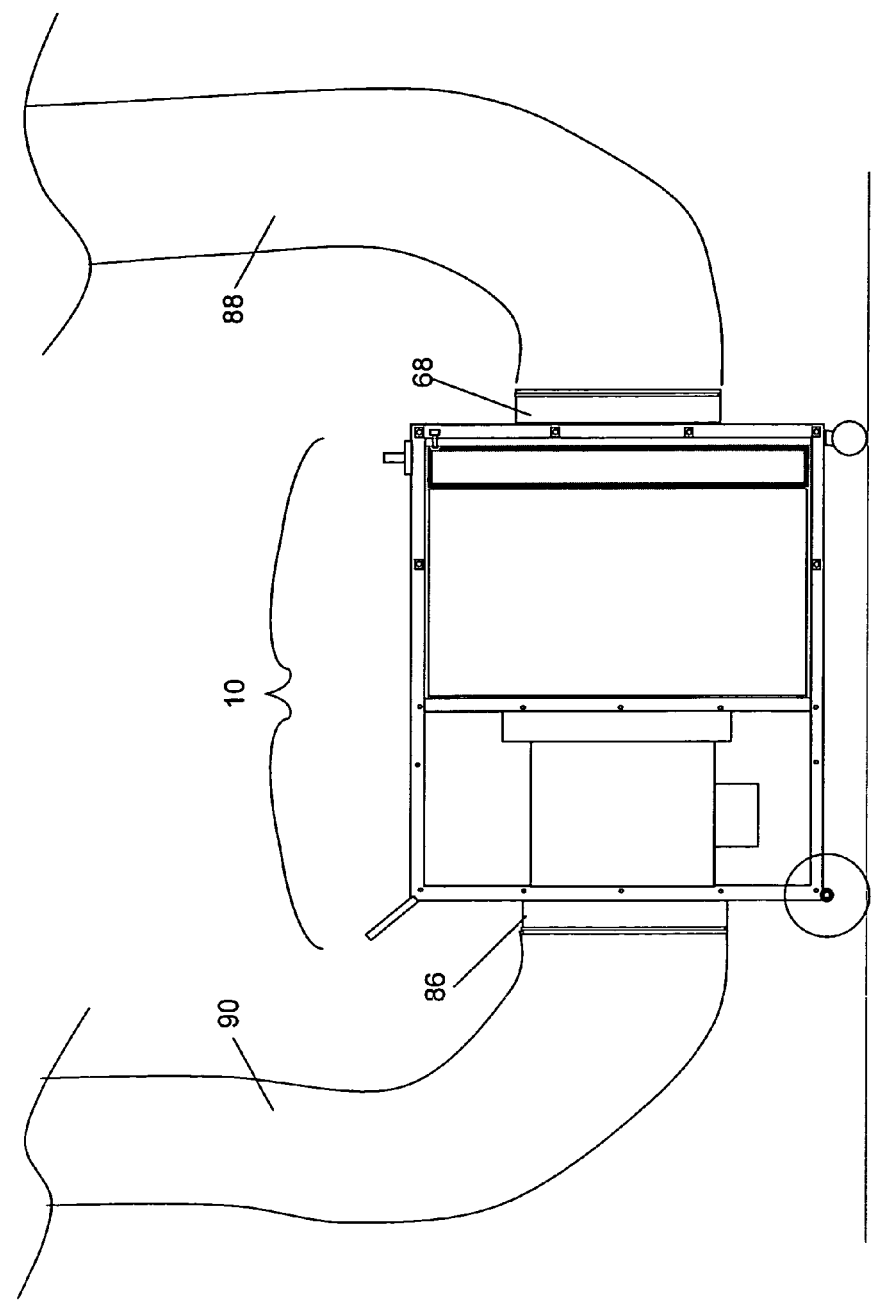
FIG. 10 is a cross sectional schematic diagram of the decontamination unit of FIG. 1 attached to ducts.

The decontamination unit 10 may also be attached to ducts, for connection to a room to be decontaminated, for example., respectively, as shown in FIG. 10. Ducts 88 and 90 are attached to the decontamination unit 10 via the duct adapters 68, 86. Preferably, the duct adapters 68, 86 provide an air tight seal between the decontamination unit 10 and the ducts 88 and 90, respectively.

Contaminated air may be drawn into the unit 10 through a duct 88 and purified air or ozone laden air may be exhausted from unit 10 through duct 90. The use of ducts 88 and 90 allow for operation of the decontamination unit 10 without exposure of the operator of the unit to the contaminants in the air or the ozone being generated. Use of the decontamination unit 10 to decontaminate rooms is discussed in more detail, below.

Figure 11:
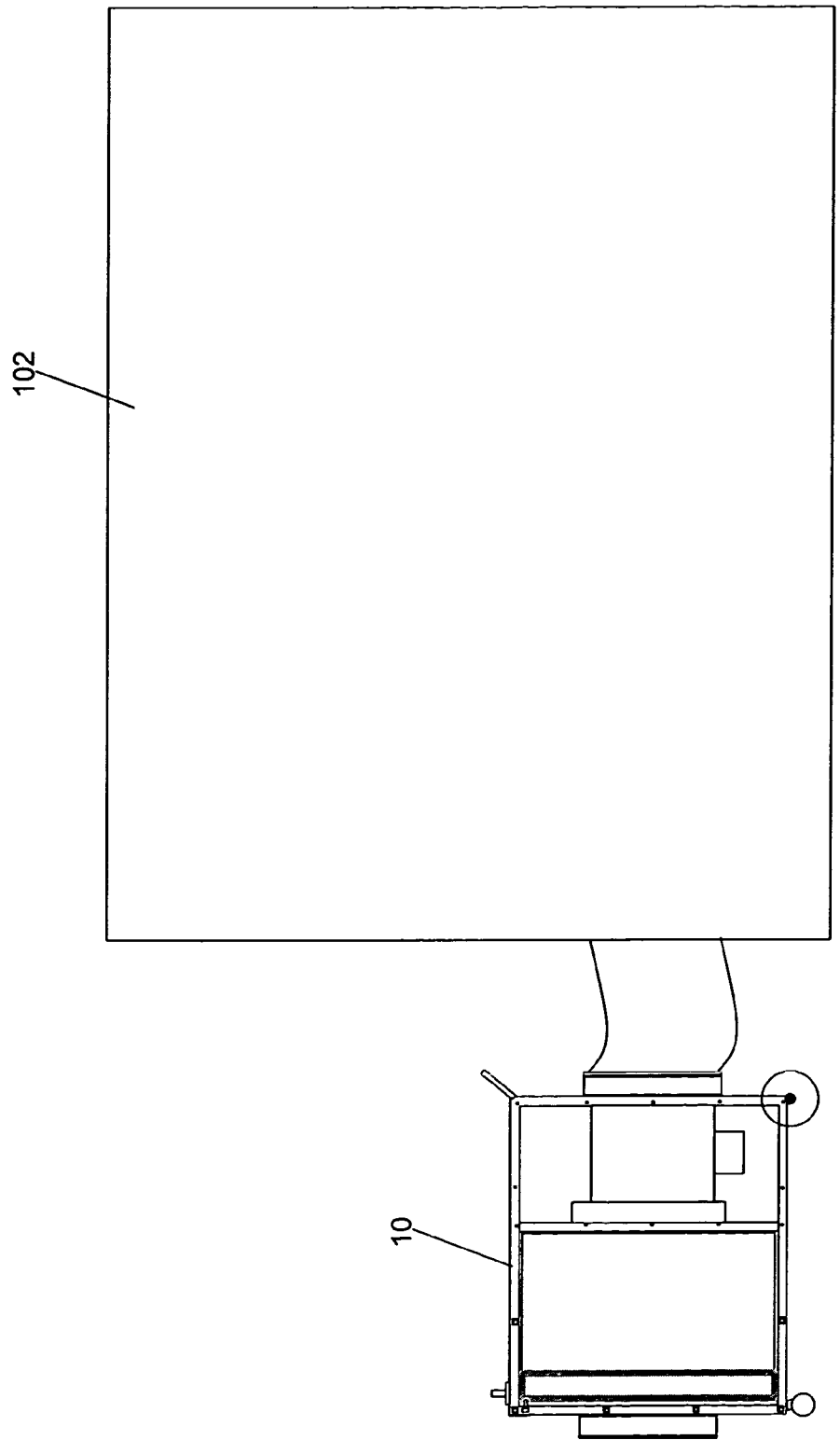
FIG. 11 is a cross sectional schematic diagram of the decontamination unit of FIG. 1, in a positive pressure application.

Preventing contaminated air from flowing into a room is essential in "clean rooms" for manufacturing delicate devices such as silica chips or for the creation of non-contaminated zones where people can be safe while decontamination is proceeding nearby. Operation of the decontamination unit 10 as shown in FIG. 11 creates a room or defined space that is essentially free of contaminated air. The decontamination unit 10 purifies contaminated air and continually pushes the purified air into a defined space 102 such that the pressure in the defined space, such as a room or hallway, increases. Because the air pressure in the defined space 102 is greater than the air pressure in its surroundings, air only flows out of the defined space 102. Accordingly, essentially no contaminated air can flow into the defined space 102.

Figure 12:
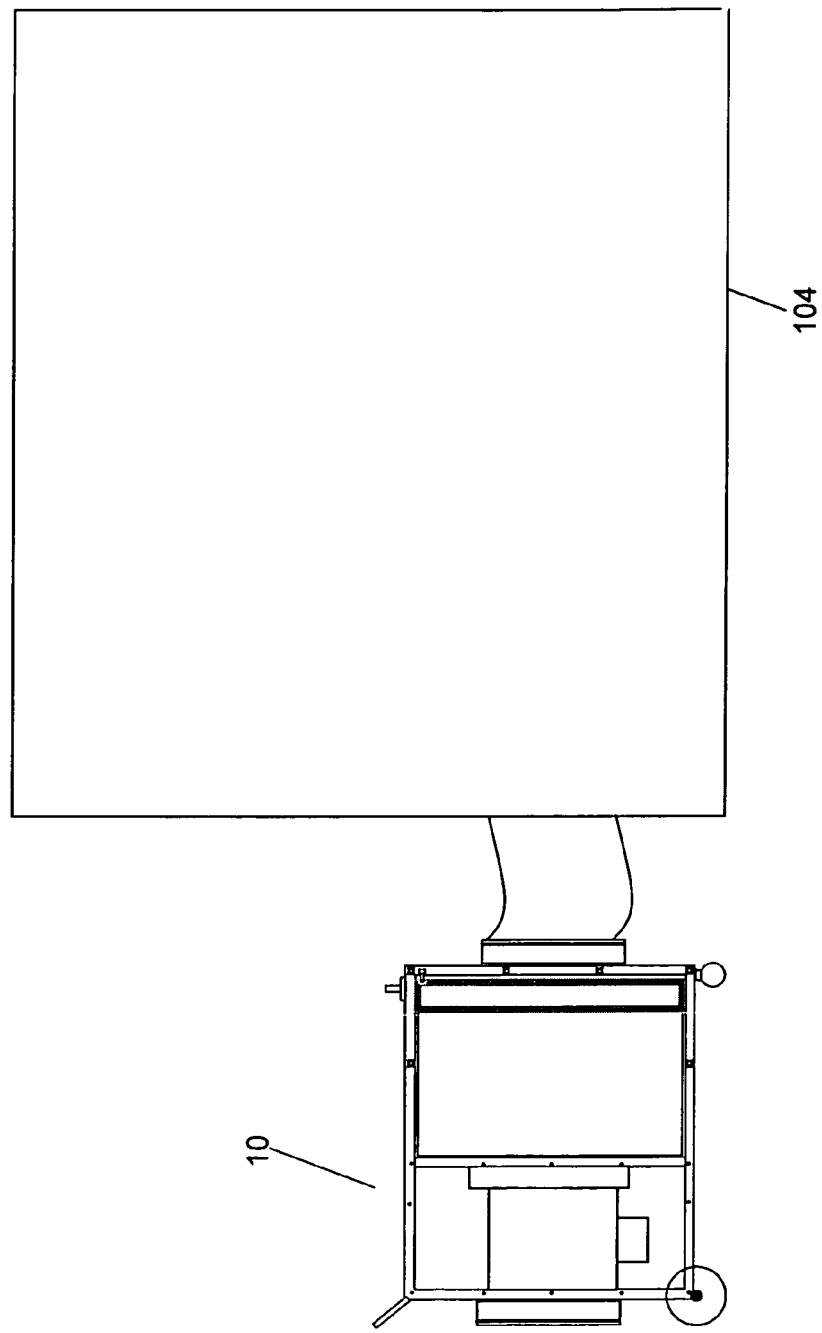
FIG. 12 is a cross sectional schematic diagram of the decontamination unit of FIG. 1, in a negative pressure application.
Figure 13:
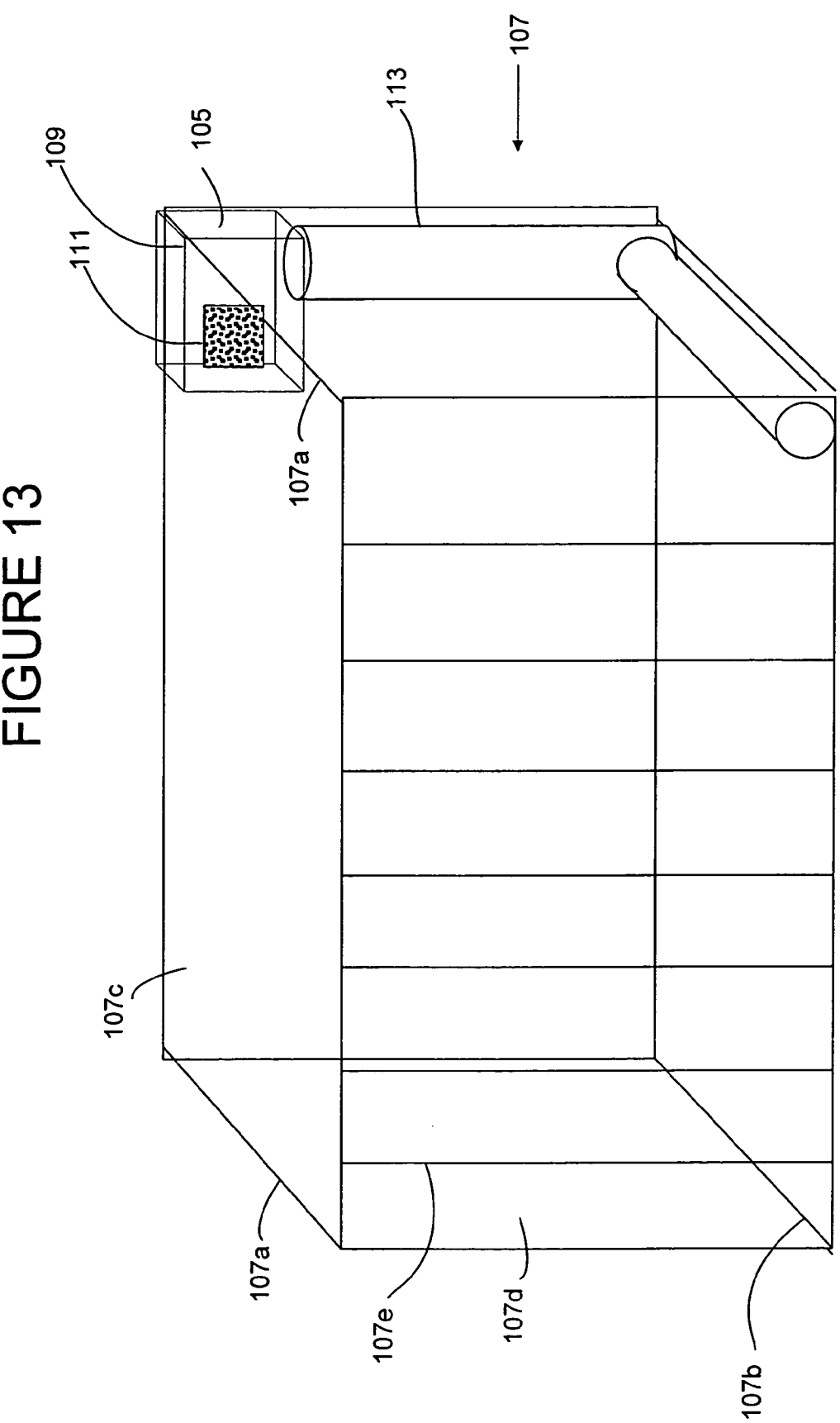
FIG. 13 is a decontamination unit in a prison cell, in accordance with another embodiment of the invention.

When a contaminant is localized to a room or defined space, preventing the spread of the contaminant is essential during decontamination. If the air pressure in the contaminated room is maintained at a level lower than the air pressure outside of the room, air will only flow into the contaminated room and contaminated air will not flow out of the room. Operation of the decontamination unit 10 under negative pressure is shown in FIG. 12 and FIG. 13. In FIG. 12 the decontamination unit 10 continually pulls contaminated air out of a defined space 104 such that the pressure in the defined space, such as a room or hallway, decreases. Because the air pressure in the defined space 104 is less than the air pressure in its surroundings, cleaner air flows from the surroundings into the contaminated space 104. The only contaminated air that can flow out of the contaminated space must go through the decontamination unit 10, which purifies the contaminated air.

FIG. 13 shows a decontamination unit 105 designed for use in a prison cell 107 containing a prisoner that may have a communicable disease. Here, the prison cell 107 comprises side walls 107a, a floor 107b, a ceiling 107c and an open front 107d with bars 107e allowing airflow into the cell. The embodiment shown draws air into the prison cell 107 and removes air from the cell to another location after filtration, via an air duct 113. This unit 105 may additionally have a tamper proof housing 109 with tamper proof screws to contain the contents of the unit, including the filter 12. Preferably, the air inlet 111 has holes smaller than 3/16 inch (4.76 millimeters) in diameter. If the decontamination unit 105 has ozone generators and can vent ozone to the outside of the prison, an ozone detector is not necessary. Alternatively, if the air is vented into the prison or prison ducting system, an ozone detector 57 is preferred. The unit 105 creates a region of low pressure in the cell 107, drawing air into the cell 107 through the bars 107e and minimizing (or preventing) air flow out of the cell through the bars. The risk of infection of people outside of the cell 107 caused by a prisoner with an airborne communicable disease may thereby be decreased.

Figure 14B:
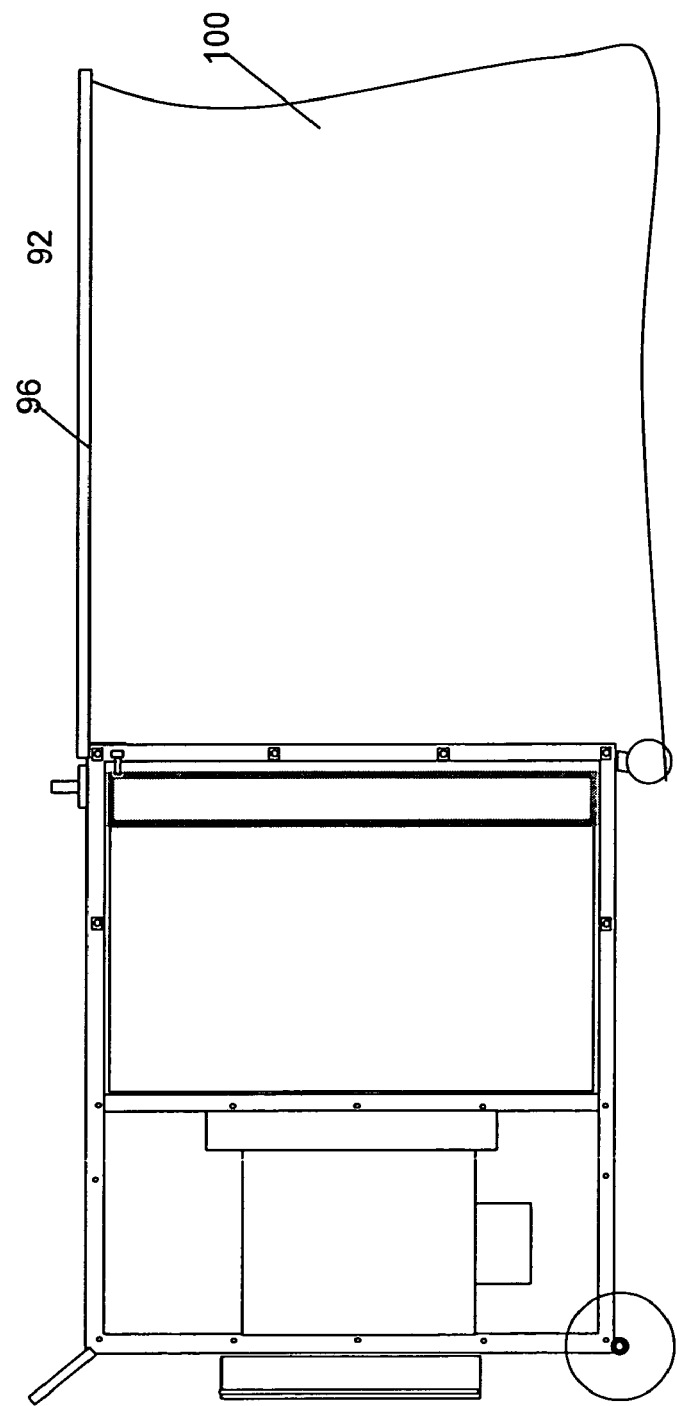

Another embodiment of the decontamination unit 10 is shown in FIGS. 14a and 14b, wherein the decontamination unit 10 includes two isolation barriers 92 and 94 attached to the side 24 of the decontamination unit 10 containing the air inlet 28, to contain local contamination, for example. Preferably, the barriers have a light weight first frame 96 and second frame 98 attached to the top of side 24. A first wall 100 hangs from first frame 96 and a second wall (not shown) hangs from second frame 98. The isolation barriers 92, 94. combined with the side 24 of the decontamination unit 10, partially enclose a space C, to maximize flow of a contaminant into the decontamination unit 11 and minimize leakage of the contaminant to the surrounding areas. A limited chemical spill in a laboratory or hospital may be quickly contained with decontamination unit 10 by placing the isolation barriers 92, 94 around the spill. The high pressure of the blower 32 draws air, including the chemical fumes from the spill, into the unit 10, preventing dissipation of the chemical fumes away from the unit 10.

In accordance with another embodiment of the invention, aspects of the germicidal filter arrangement of the decontamination unit 10 are combined with a movable isolation device as described in U.S. Pat. No. 6,162,118 (referred to as the '118 patent), which is incorporated herein by reference, as shown in FIGS. 15-19. In FIGS. 15-19, elements common to earlier embodiments are commonly numbered.

A mobile isolation device 106 for infectious patients in accordance with this embodiment may provide negative pressure containment, as described above, in a partially enclosed space 108 defined by the device 106. Negative pressure is applied to the partially enclosed space 108 to cause air to flow into the partially enclosed space containing a patient and to prevent or decrease the escape of infectious agents from the space.

A preferred configuration of this embodiment of the invention improves upon the disclosure of the mobile isolation device in the '118 patent by providing a germicidal killing zone in the filter 12 by illuminating the upstream 44 and downstream 46 sides of the filter by germicidal UV 52 and optionally permeating the filter 12 with germicidal levels of ozone, as described above. In addition, in the preferred configuration, a recycling vent 110 or duct is provided to return some of the purified air 112 back into the enclosed space 108. About 50% to about 75% of the purified air may be recycled, for example. The return of purified air 112 for recycling in the enclosed space 108 decreases the amount of air coming into the enclosed space from the air in the hospital or other such location where the isolation device is located, minimizing exposure of the patient to additional infectious agents. Since many patients placed in isolation have compromised immunity or have respiratory complications, recycling purified air to the patient may provide significant protection to the patient. While it is preferred to provide both the filter 12 as a germicidal killing zone and the recycling vent 110, either aspect of the invention may be advantageously used in an mobile isolation unit. Recycling of filtered air may be used in the non-mobile decontamination and isolation units, as well.

The isolation device 106 has an air conducting unit 114 for air flow. The unit 114 has a primary duct 116 with an internal wall 118, an external wall 120, two side walls 122 and 124, and bottom wall 126. The bottom 126 of the primary duct 116 is attached to a frame 128 supporting the air conducting unit on wheels 130 or skid bars.

The top of the primary duct 116 is attached to an overhanging duct 132 that hangs forward of the internal wall 118. The overhanging duct 132 has a second internal wall 134, a second external wall 136, two second side walls 138 and 140, a front wall 142 and a back wall 144. The overhanging duct 132 has an air inlet 146 and the primary duct 116 has an air outlet 148 so that air can flow from the air inlet 146 through the overhanging duct 132 into the primary duct 116 and out the primary duct 116 at the air outlet 148. Preferably, the air conducting unit 114 is airtight except at air inlets 146 and air outlets 148. Alternatively, an overhanging barrier wall may replace the overhanging duct 132 and the air inlet 146 may be placed in the internal wall 118 of the primary duct 116 near the top. Additionally, the air inlet 146 may be an overhanging tubular frame 150 with a plurality of holes 152 along the bottom of the frame, wherein the frame defines the top edges of the partially enclosed space 108.

The overhanging frame 150 may be attached to the side walls 122 and 124 of the primary duct 116 at the top of the walls. The frame 150 may extend along the front 142 and second sides 138 and 140 of the overhanging duct 132, and provides support for the duct 132. In the preferred embodiment of the present invention, the frame 150 comprises tubular members, to minimize the weight of the isolation device. The isolation device is therefore more easily moved from one location to another. In one such embodiment of the present invention, a tubular member 150 with a plurality of holes 152 therethrough is used to make the top portion of the frame 151. When such a tubular member 150 is provided, the primary duct 116 may be connected to the tubular member so that air can be conducted between the partially enclosed space and the outside location through the tube holes 152, the tubular member and the primary duct 116. If enough tube holes 152 are provided in the tubular member, portions of the barrier may be omitted because air flowing into the tube holes 152 provides protection against disease carrying objects exiting the partially enclosed space.

Figure 15:
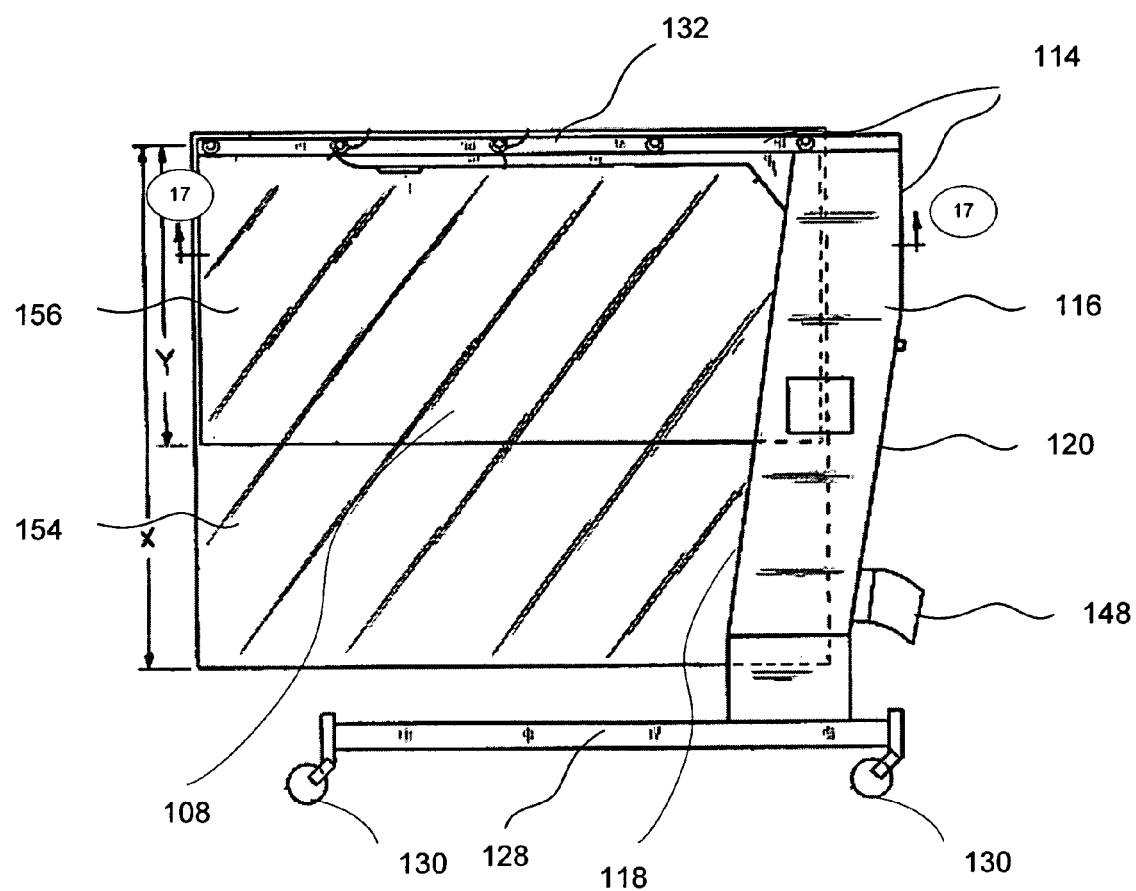
FIG. 15 is a cross sectional schematic diagram of a mobile isolation unit in accordance with another embodiment of the invention.

At least one translucent wall is supported by the overhanging duct 173, to define in part the partially enclosed space 108. Preferably, a pair of parallel translucent walls 154, 156 hang from each side of the overhanging duct 132 or overhanging barrier. An inner wall 156 is preferably shorter than an outer wall 154. As shown in FIG. 15, the inner wall 156 has a length Y and the outer wall has a longer length X. If an overhanging support frame 150 is present, the translucent walls 154 and 156 may hang from the sides of the support frame 150. In this example, the partially enclosed space 108 is defined by the internal wall 118 of the primary duct 116, the second internal wall 134 of the overhanging duct 132 or barrier and the two translucent walls 154 and 156. Preferably, the translucent walls 154, 156 are flexible. A healthcare professional may then move the outer, longer wall 156 out of the way to access a patient contained in the partially enclosed space, while the shorter, inner wall 154 still provides a barrier between the doctor and the patient.

As described above, a blower 32 is attached within the primary duct 116 to pull air into the air inlet 146 and push air out of the air outlet 148. A filter 12 is fixed within the housing such that the air flowing from the air inlet 146 to the air outlet 148 during operation of the blower must pass through the filter 12. The filter may be a V-bank filter, as described with respect to FIG. 3, for example. UV lamps 50, 54 are preferably provided, and lamps 50 may be an ozone generator or another ozone generator may be provided, as is also described above.

The mobile isolation unit 106 may also have a prefilter 60 attached to the air conducting unit 114 upstream of the UV lamps 50. The prefilter 60 can be placed in a sleeve framing the air inlet 146 or fixed within the housing downstream of the air inlet 146 and upstream of the UV lamps 50. Choice of prefilter may depend upon the type(s) of contaminants known or anticipated to be in the air, as discussed above. Optionally, more than one prefilter may be inserted into the air conducting unit. The filter is preferably an ULPA filter, as described above.

Figure 16:
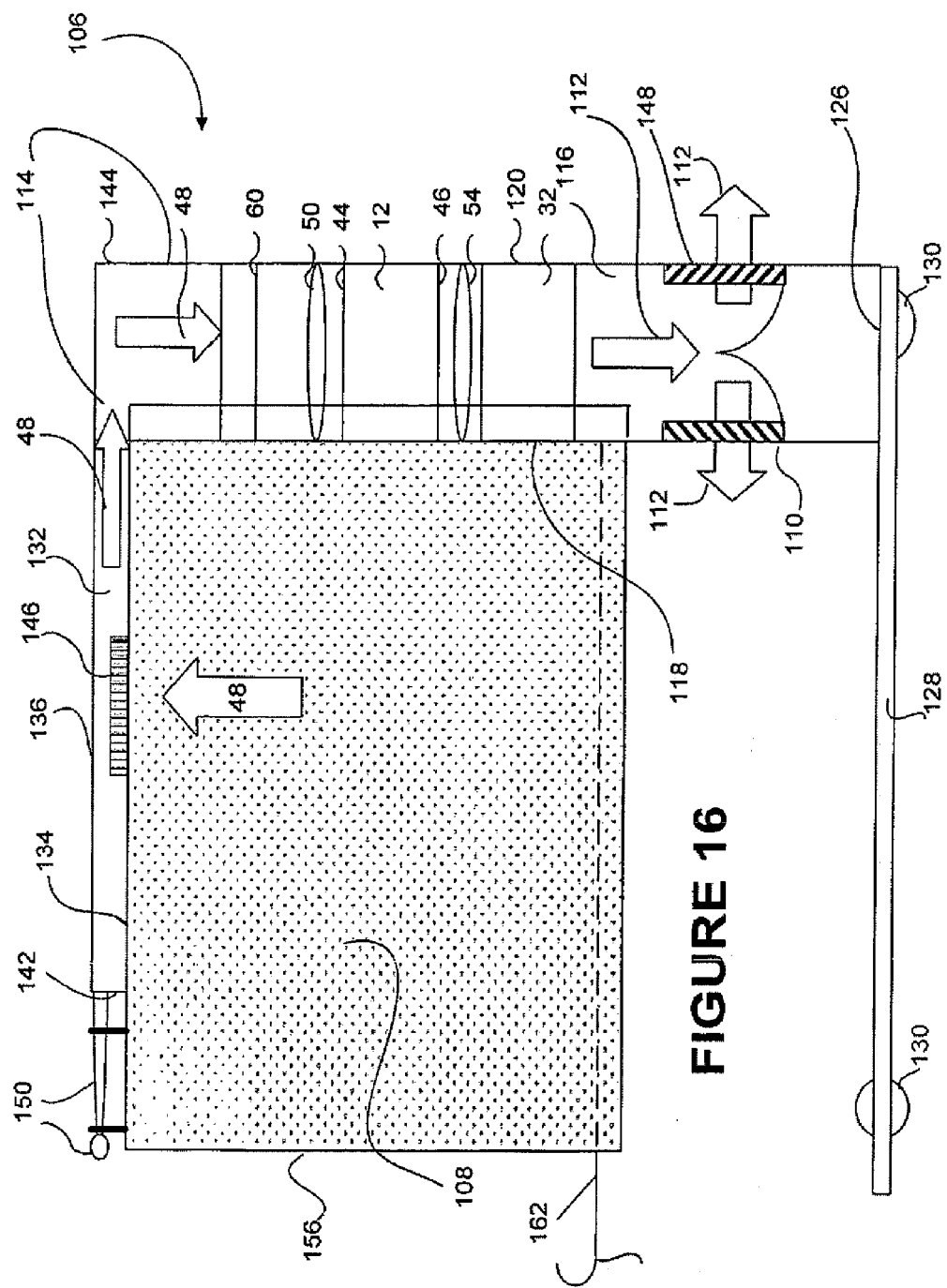
FIG. 16 is a cross sectional schematic diagram of the mobile isolation unit of FIG. 15, with a portion of the air conducting unit and frame removed.
Figure 17:
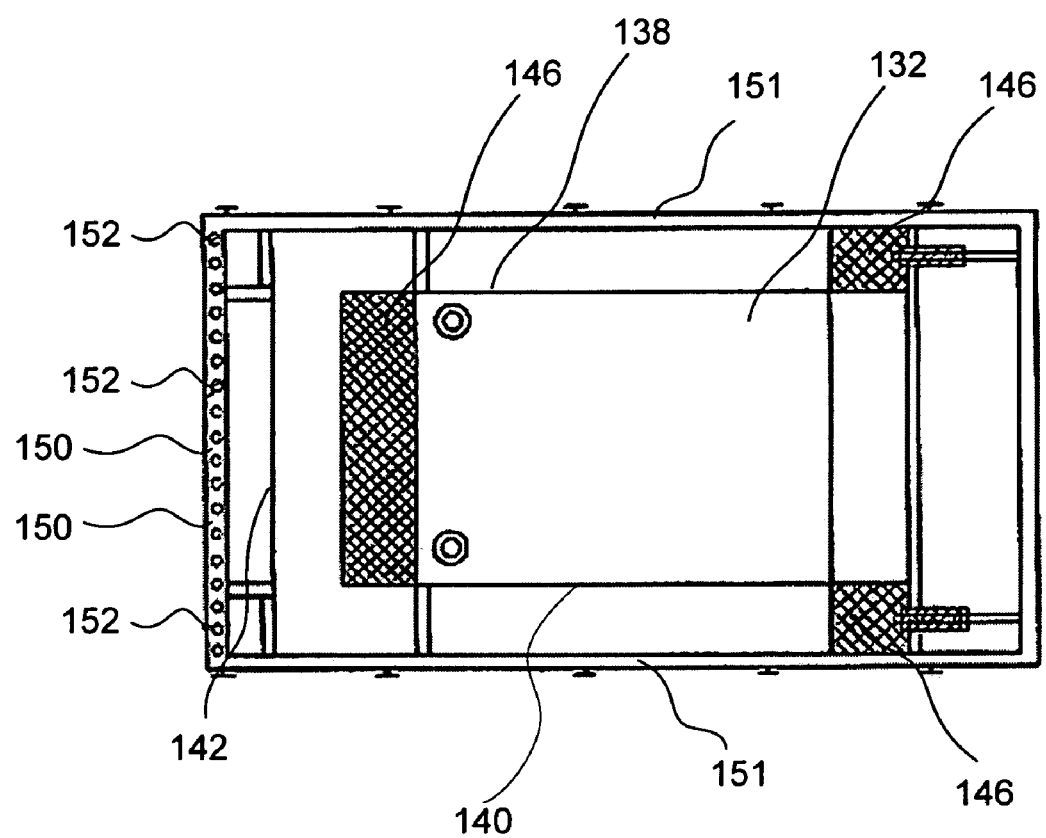
FIG. 17 is the cross sectional schematic diagram of the mobile isolation unit of FIG. 15, taken along the lines 17-17.
Figure 18:
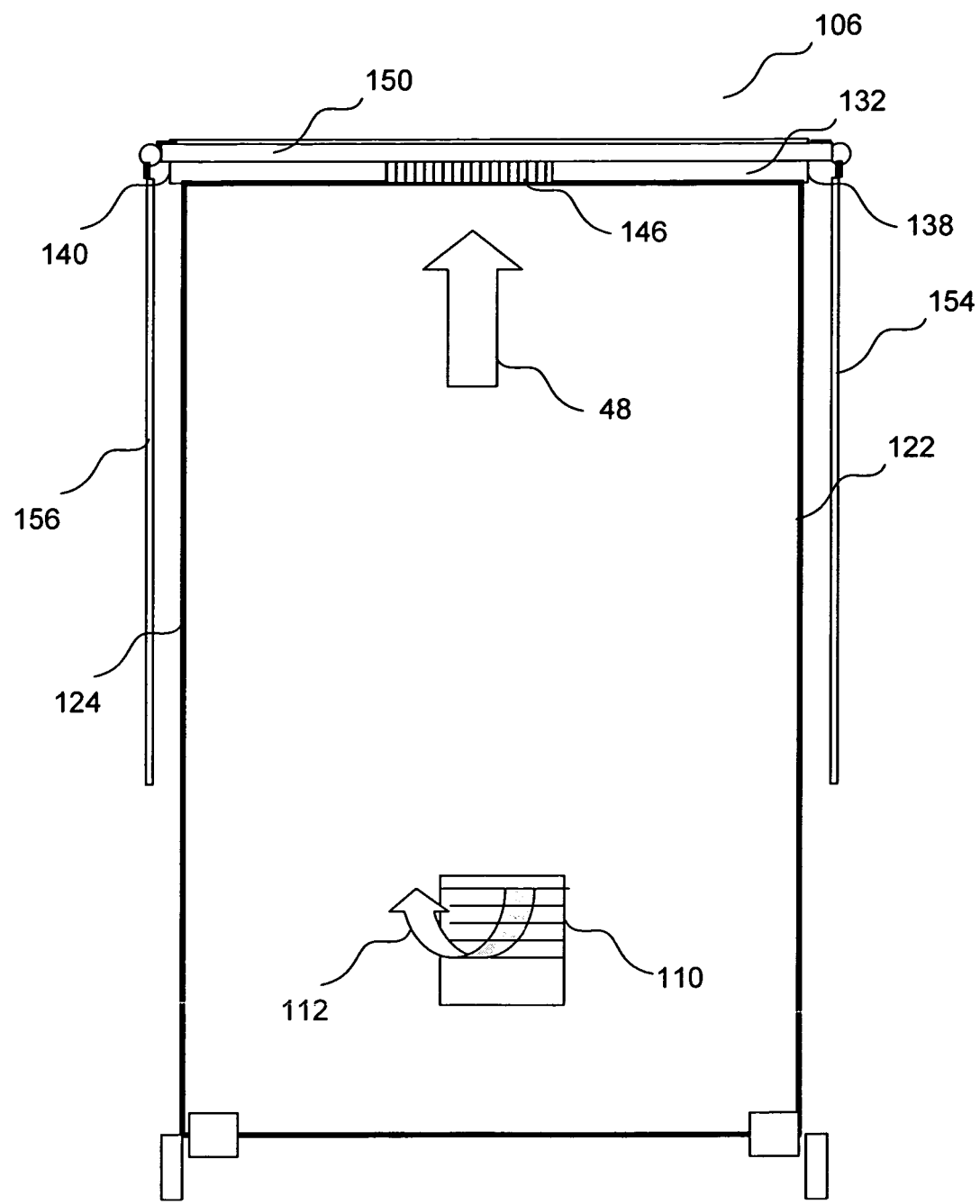
FIG. 18 is a front view of a mobile isolation unit.

The blower 32 blows filtered air 112 out the air outlet 148. The air outlet 148 may not be in the internal wall 118 of the primary duct 116 which faces the partially enclosed space 108. Proper functioning of the isolation device 106 requires negative pressure in the partially enclosed space 108 and therefore air preferably exits the device to an outside location. As mentioned above, a recycling vent 110 in the interior wall 118 of the primary duct 116 proximate to the enclosed space 108 may be provided to supply a portion of the filtered air 112 exiting the duct 116 back to the partially enclosed space 108, as shown in FIG. 16. The recycling vent 110 may supply the air into or below the partially enclosed space 108.

Figure 19:
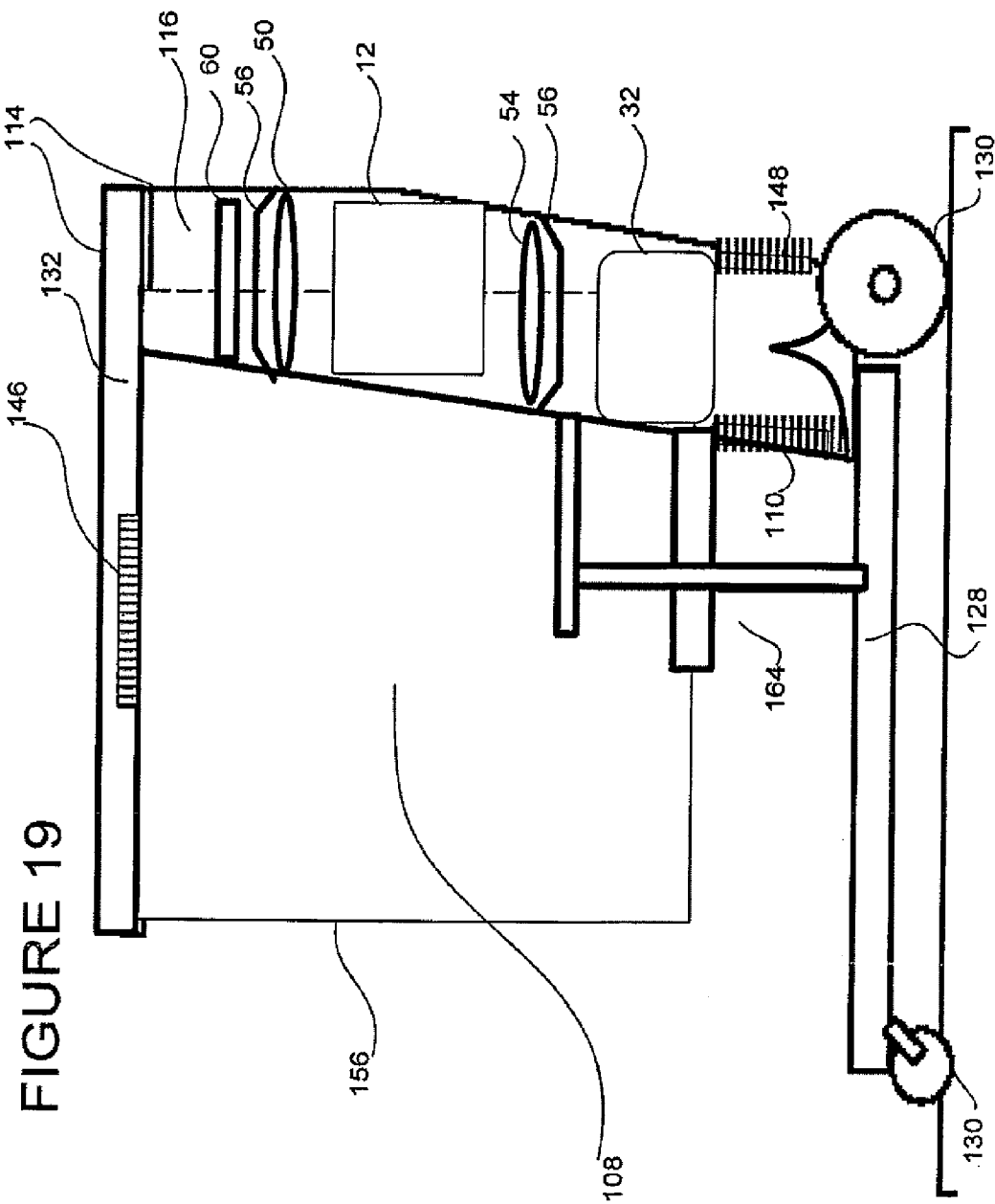
FIG. 19 is a cross sectional schematic diagram of a wheelchair isolation unit, in accordance with another embodiment of the invention.

A patient may be supported by a bed 162 wholly or partially within the partially enclosed space 18, as shown in FIG. 16. The patient may also be supported in a chair 164 so that the patient is wholly or partially within the space 108, as shown in FIG. 19. The chair 164 is positioned so that a person sitting upon the chair 164 is at least partially within the partially enclosed space 108. The chair is attached to and supported by a frame 128 connected to the bottom of the air conducting unit 114, so that the unit functions as a wheelchair, as well. The chair 164 may also be supported by the internal wall 118. Preferably, the chair is capable of being folded against the internal wall 118 or supporting frame 128, when not in use. Folding chairs are well-known and widely available. A rechargeable battery may be provided to power the filtration system. An inverter may be provided to convert DC voltage (12 volts, for example) provided by the battery to AC (117 volts, 60 cycles, for example). Movement of highly contagious patients in a hospital may thereby be facilitated.

In the embodiments of FIGS. 15-19, in order to provide adequate protection from the spread of infectious disease, the filter 12 and blower 32 are preferably sized to move at least about 600 CFM (16.99 cubic meters per minute). In one example, the velocity of the airflow past the patient and out of the partially enclosed space 108 is at least about 175 feet (53.34 meters) per minute. Air flow of this magnitude is believed to be sufficient to prevent the spread of infectious agents outside of the partially enclosed space 108 containing the patient.

What is claimed is:

1. A decontamination device comprising:
    a housing defining an air inlet, an air outlet and a path for air to flow from the inlet to the outlet;
    a stationary filter positioned within the housing, along the path, the filter having an upstream side defining a plurality of adjacent, upstream facing chambers across the upstream side to receive air flowing along the path, and a downstream side defining a plurality of adjacent, upstream facing chambers across the downstream side for the exit of air from the filter to the path;
    a plurality of first stationary ultraviolet lamps, wherein at least some of the plurality of first lamps are at least partially within respective upstream facing chambers to directly and simultaneously illuminate the entirety of each of the respective upstream facing chambers;
    a plurality of second stationary ultraviolet lamps, wherein at least some of the plurality of second lamps are at least partially within respective downstream facing chambers to directly and simultaneously illuminate the entirety of each of the respective downstream facing chambers; and
    an ozone generator proximate the filter.

2. The decontamination device of claim 1, further comprising:
    a blower within the housing, along the path, to cause air to flow along the path during operation.

3. The decontamination device of claim 2, further comprising:
    a manually operated control device supported on an exterior surface of the housing; and
    the control device being coupled to the ozone generator, to the blower and to at least one of the second UV lamps to control activation of the ozone generator, the blower and the second UV lamp.

4. The decontamination device of claim 1, further comprising a second ozone generator downstream of the filter.

5. The decontamination device of claim 4, further comprising:
    a manually operated control device supported on an exterior surface of the housing;
    the control device being coupled to the second ozone generator to control operation of the second ozone generator.

6. The decontamination device of claim 4, further comprising:
    a timer coupled to the second ozone generator to control operation of the second ozone generator.

7. The decontamination device of claim 1, further comprising:
    a manually operated control device supported on an exterior surface of the housing; and
    the control device being coupled to the ozone generator to control operation of the ozone generator.

8. The decontamination device of claim 1, further comprising at least one prefilter positioned along the path, upstream of the first ultraviolet lamps, such that air flows through the at least one prefilter prior to flowing through the filter, during operation.

9. The decontamination device of claim 1, wherein the ozone generator is an ultraviolet lamp.

10. The decontamination device of claim 1, further comprising:
    at least one reflector positioned to reflect light from at least one of the first and second ultraviolet lamps onto a surface of the filter.

11. The decontamination device of claim 10, further comprising:
at least one first reflector positioned to reflect light from at least one of the first ultraviolet lamps onto at least one of the upstream facing chambers of the filter; and
at least one second reflector positioned to direct ultraviolet light from at least one of the second ultraviolet lamps onto at least one of the downstream facing chambers of the filter.

12. The decontamination device of claim 1, wherein:
the filter comprises a plurality of transverse intersecting walls forming at least one upstream facing V-shaped region and at least one downstream facing V-shaped region;
each upstream facing V-shaped region is directly, completely illuminated by at least one of the first ultraviolet lamps during operation; and
each downstream facing V-shaped region is directly, completely illuminated by at least one of the second ultraviolet lamps during operation.

13. The decontamination device of claim 1, wherein:
the housing has an external wall defining at least one air sampling port through the wall, to provide communication from an exterior of the housing to the path.

14. The decontamination device of claim 1, further comprising an intake duct adapter fixed to the housing, proximate the air inlet.

15. The decontamination device of claim 1, further comprising an exhaust duct adapter fixed to the housing, proximate the air outlet.

16. The decontamination device of claim 1, wherein the filter removes at least 99.97 percent of particles of 0.3 micron size during operation.

17. The decontamination device of claim 16, wherein the filter removes at least 99.99 percent of particles of 0.1 micron size during operation.

18. The decontamination device of claim 1, wherein the filter comprises ultraviolet transmissive material.

19. The decontamination device of claim 1, wherein the filter comprises fire resistant material.

20. The decontamination device of claim 1, wherein at least one of the second ultraviolet lamps emits radiation capable of breaking down ozone during operation.

21. The decontamination device of claim 20, further comprising:
a manually operated control device supported on an exterior of the housing; and
the control device being coupled to at least one of the second ultraviolet lamps to control operation of the second ultraviolet lamp.

22. The decontamination device of claim 1, further comprising:
an ozone detector proximate to the air inlet; and
a control device being coupled to the ozone detector to control operation of the ozone generator.

23. The decontamination device of claim 1, further comprising:
a high efficiency gas absorber coupled to the inlet.

24. A decontamination device comprising:
a housing defining an inlet, an outlet, and a path for air to flow from the inlet to the outlet;
a stationary filter positioned along the path to filter air flowing along the path, the filter comprising a plurality of transverse intersecting walls defining a plurality of upstream facing V-shaped chambers to receive air along the path, and a downstream side for air to exit from the filter, to the path; and
at least one stationary ultraviolet lamp upstream of the filter, at least partially within a respective region defined by each V-shaped chamber, to completely, directly and continuously illuminate each transverse wall of a respective V-shaped chamber.

25. The decontamination device of claim 24, further comprising:
a blower within the housing, along the path, to cause air to flow along the path during operation.

26. The decontamination device of claim 24, wherein the downstream side of the filter defines at least one downstream facing chamber, the unit further comprising:
at least one second ultraviolet lamp downstream of the filter, facing the at least one downstream facing chamber, to completely, directly illuminate the at least one downstream facing chamber.

27. The decontamination device of claim 26, further comprising:
at least one second reflector downstream of the at least one second ultraviolet lamp, to reflect ultraviolet light emitted by the at least one second ultraviolet lamp, onto the at least downstream facing chamber.

28. The decontamination device of claim 27, wherein the at least one second ultraviolet lamp is within a second region defined by the downstream facing chamber.

29. The decontamination device of claim 24, further comprising:
an ozone generator proximate the filter.

30. The decontamination device of claim 24, further comprising:
a prefilter along the path, upstream of the filter.

31. The decontamination device of claim 24, wherein the filter removes at least 99.97 percent of particles of 0.3 micron size, during operation.

32. The decontamination device of claim 24, wherein the filter comprises ultraviolet transmissive material.

33. The decontamination device of claim 24, wherein the filter is fire resistant.

34. The decontamination device of claim 24, wherein the housing has an external wall defining an air sampling port through the wall, enabling communication between an exterior of the housing and the path.

35. The decontamination device of claim 24, further comprising:
at least one reflector upstream of each ultraviolet lamp, to reflect ultraviolet radiation emitted by each ultraviolet lamp, onto each transverse wall of the respective V-shaped chamber.

36. A decontamination device comprising:
a housing defining an inlet, an outlet, and a path for air to flow from the inlet to the outlet;
a filter positioned along the path to filter air flowing along the path, the filter having an upstream side defining at least one upstream facing chamber within the filter to receive air along the path, and a downstream side for air to exit from the filter, to the path; and
at least one ultraviolet lamp upstream of the filter, positioned at least partially within a region defined by the chamber, to completely and simultaneously illuminate the chamber.

37. The decontamination device of claim 36, further comprising:
a blower to cause air to flow along the path.

38. An air decontamination device comprising:
- a housing defining an air inlet, an air outlet and a path for air to flow from the inlet to the outlet;
- a filter comprising a plurality of transverse walls defining, at least in part, at least one upstream facing V-shaped chamber to receive air flowing along the path, and at least one downstream facing V-shaped chamber for the exit of air from the filter, to the path;
- at least one ultraviolet lamp stationary with respect to the filter, each of the at least one ultraviolet lamps being at least partially within each V-shaped chamber, to directly and completely illuminate each transverse wall defining a respective V-shaped chamber; and
- at least one reflector stationary with respect to the filter, positioned and configured to reflect ultraviolet light from each ultraviolet lamp toward a respective V-shaped chamber at a plurality of angles, to completely illuminate each transverse wall defining the V-shaped chamber.

39. The air decontamination device of claim 38, wherein the blower is downstream of the filter.

40. The air decontamination device of claim 38, further comprising:
- at least one ozone generator proximate the filter.

41. The air decontamination device of claim 38, further comprising:
- an ozone detector proximate to the air inlet; and
- the ozone detector being coupled to the at least one ozone generator to control operation of the ozone generator.

42. The decontamination device of claim 38, further comprising:
- at least one prefilter positioned along the path, upstream of the filter, such that air flows through the at least one prefilter prior to flowing through the filter, during operation.

43. The air decontamination device of claim 38, wherein:
- the housing has an external wall defining at least one air sampling port through the wall, to provide communication from an exterior of the housing to the path, to draw air from the exterior of the housing, through the port, to the path.

44. The decontamination device of claim 43, further comprising at least one of:
- at least one sampling tube received within the at least one air sampling port, to collect air external to the housing; and
- at least one particulate collector received within the at least one port, to collect particles in the air external to the housing.

45. The air decontamination device of claim 38, wherein the filter removes at least 99.99 percent of particles of 0.1 micron size during operation.

46. The air decontamination device of claim 38, wherein the filter comprises ultraviolet translucent material.

47. The air decontamination device of claim 46, wherein the filter comprises fiberglass.

* * * * *